US012767654B2

(12) United States Patent
Kameshwar et al.

(10) Patent No.: US 12,767,654 B2
(45) Date of Patent: *Oct. 20, 2026

(54) 2-(4-(2-(7,8-DIMETHYL-[1,2,4]TRIAZOLO[1,5-A]PYRIDIN-6-YL)-3-ISOPROPYL-1H-INDOL-5-YL)PIPERIDIN-1-YL)ACETAMIDE SALT AND CRYSTALLINE FORMS THEREOF

(71) Applicant: Bristol-Myers Squibb Company, Princeton, NJ (US)

(72) Inventors: Prashant Mrityunjaya Sujata Kameshwar, Karnataka (IN); Roopa Narasimhamurthy, Karnataka (IN); Qi Gao, Princeton, NJ (US); Jennifer Nelson, West Lafayette, IN (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/634,579

(22) Filed: Mar. 31, 2026

(65) Prior Publication Data

US 2026/0248779 A1 Aug. 27, 2026

Related U.S. Application Data

(63) Continuation-in-part of application No. PCT/US2024/055605, filed on Nov. 13, 2024.

(60) Provisional application No. 63/598,181, filed on Nov. 13, 2023.

(51) Int. Cl.
*A61K 31/4545* (2006.01)

(52) U.S. Cl.
CPC ................................ *A61K 31/4545* (2013.01)

(58) Field of Classification Search
None
See application file for complete search history.

(56) References Cited

FOREIGN PATENT DOCUMENTS

| | | | | | |
|---|---|---|---|---|---|
| WO | 2018005586 | A1 | | 1/2018 | |
| WO | WO-2020227337 | A1 | * | 11/2020 | ................ C07F 9/09 |
| WO | WO-2021252718 | A1 | * | 12/2021 | ........... A61K 31/437 |

OTHER PUBLICATIONS

Swarbrick, et al., Encyclopedia of Pharmaceutical Technology 13 (Marcel Dekker, NY 1996), pp. 453-499.
International Search and written opinion issued in PCT/US2024/055605 on Nov. 2, 2025.
Brittain H.G., et al., "Polymorphism in Pharmaceutical Dosage Forms," Drugs and the Pharmaceutical Sciences, 1999, 210 pages.

* cited by examiner

*Primary Examiner* — Kortney L. Klinkel
*Assistant Examiner* — Alison Azar Hastings
(74) *Attorney, Agent, or Firm* — Blank Rome LLP

(57) ABSTRACT

Disclosed are salts of 2-(4-(2-(7,8-dimethyl-[1,2,4]triazolo[1,5-a]pyridin-6-yl)-3-isopropyl-1H-indol-5-yl)piperidin-1-yl)acetamide and crystalline forms thereof. The compounds of the invention are useful as treatments for lupus.

20 Claims, 8 Drawing Sheets

PXRD of Form M (MSA Salt P49 also known as P10)

2-(4-(2-(7,8-DIMETHYL-[1,2,4]TRIAZOLO[1,5-A]PYRIDIN-6-YL)-3-ISOPROPYL-1H-INDOL-5-YL)PIPERIDIN-1-YL)ACETAMIDE SALT AND CRYSTALLINE FORMS THEREOF

CROSS REFERENCE

This application is a continuation-in-part of International Patent Application No. PCT/US2024/055605, filed Nov. 13, 2024, which claims the benefit of U.S. Provisional Application Ser. No. 63/598,181 filed Nov. 13, 2023, each of which is incorporated herein in its entirety.

FIELD OF THE INVENTION

The present invention generally relates to salts of 2-(4-(2-(7,8-dimethyl-[1,2,4]triazolo[1,5-a]pyridin-6-yl)-3-isopropyl-1H-indol-5-yl)piperidin-1-yl)acetamide and crystalline forms thereof.

BACKGROUND OF THE INVENTION

The compound, 2-(4-(2-(7,8-dimethyl-[1,2,4]triazolo[1,5-a]pyridin-6-yl)-3-isopropyl-1H-indol-5-yl) piperidin-1-yl)acetamide has the structure of Formula (I):

(I)

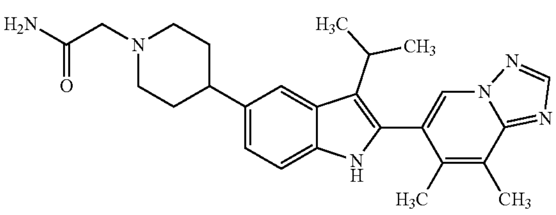

and is referred to herein as "Compound (I)". Compound (I) is disclosed as Example 15 in WO 2018/005586 A1, which is assigned to the present assignee. Compound (I) has the generic name afimetoran.

Compound (I) is an inhibitor of Toll-like receptor 7 and 8 (TLR7/8) and is currently in clinical trials for the treatment of lupus.

In the synthesis of a chemical compound intended for pharmaceutical use, it is necessary to isolate and purify the compound at the completion of the synthetic process and prior to further processing to provide the compound in a pharmaceutical formulation. The isolation and the purification steps, which can be combined or separate consecutive steps, provide the compound as a purified solid with minimal loss of yield during isolation from other components of the reaction mixture and/or during purification to remove impurities from the isolated compound sample.

In preparing a pharmaceutical composition, a salt and/or a form of the active ingredient is sought that has a balance of desired properties, such as, for example, dissolution rate, solubility, bioavailability, and/or storage stability. For example, a salt and/or a form of the active ingredient is sought having sufficient stability, solubility, and bioavailability to prevent the salt and/or form converting during manufacture, preparation, and/or storage of the pharmaceutical composition to another form having an undesirable solubility and/or bioavailability profile. For example, a salt is sought that does not undergo disproportionation. Also sought is a crystalline form of the salt that is stable and has low hygroscopicity at ambient temperature and humidity conditions.

The usefulness of an oral formulation is dependent upon, among other things, the degree to which the active agent is bioavailable and consistency in bioavailability among patients. The bioavailability of orally administered drugs is often affected by various factors including, for example, the solubility of the drug in the gastrointestinal tract, the stability of the drug in the gastrointestinal tract, and drug absorption in the gastrointestinal tract. Further, these factors may be affected by coadministration of other drugs and/or the intake of food, which may lead to variability in the bioavailability of orally administered drugs.

The aqueous solubility and dissolution rate of a compound can be dependent on the pH of the aqueous medium. A compound can have a higher or a lower dissolution rate at pH values below 5 than at a pH value of 7. In the oral administration of the compound, the dissolution rate and hence the bioavailability of the compound can be affected by the pH of the stomach contents. The normal pH of the stomach is 1.2 to 1.8 according to C. J. Perigard, *Clinical Analysis*, Chapter 32, in *Remington: The Science and Practice of Pharmacy* $20^{th}$ Edition, A. R. Gennaro, editor; 2000, Lippinocott Williams & Wilkins, Baltimore, MD. However, patients often take other medications that can raise the pH of the stomach, including antacids, proton pump inhibitors, and H2-receptor antagonists such as famotidine, which can lower the dissolution rate of the compound.

The pH of the stomach also changes with the consumption of food. Hence, the solubility, dissolution rate, and bioavailability can vary upon the oral administration of a compound either before a meal (fasting state) or after a meal (feed state).

It is desirable to provide a solid form that can be reproducibly produced from the isolation and/or purification steps.

Further, it is desirable to isolate the purified compound in a solid form that is physically and chemically stable at a range of storage conditions, such as at different conditions of temperature and humidity.

Furthermore, it is desirable to provide a salt of the compound that can be administered in oral drug compositions that mitigates or minimizes changes in dissolution rates as a result of variations in stomach or intestinal pH values.

Still, furthermore, it is desirable to provide a salt of the compound that can be administered in an oral drug composition in a form that provides reliable and reproducible plasma concentrations following administration to a patient.

The Applicants have found at least one salt of Compound (I) that is physically and chemically stable at a range of storage conditions.

Further, the Applicants have found at least one crystalline form of a salt of Compound (I) that surprisingly provides Compound (I) in a solid form that is physically and chemically stable at a range of storage conditions.

The Applicants have found at least one salt of Compound (I) that surprisingly reduces the variability in the bioavailability of Compound (I) and reduces the variability of the bioavailability of Compound (I) as a result of variations in stomach or intestinal pH values.

The Applicants have found at least one crystalline form of a salt of Compound (I) that surprisingly reduces the variability in the bioavailability of Compound (I), reduces the variability of the bioavailability of Compound (I) as a result of variations in stomach or intestinal pH values, and has suitable physically and chemically stable at a range of storage conditions.

The present invention is also directed to other important aspects.

SUMMARY OF THE INVENTION

The present invention provides Compound (I) as a benzenesulfonic acid salt, a hydrobromic acid salt, hydrochloric acid salt, citric acid salt, and a methane sulfonic acid, and crystalline forms thereof.

DETAILED DESCRIPTION OF THE INVENTION

Figure 1:
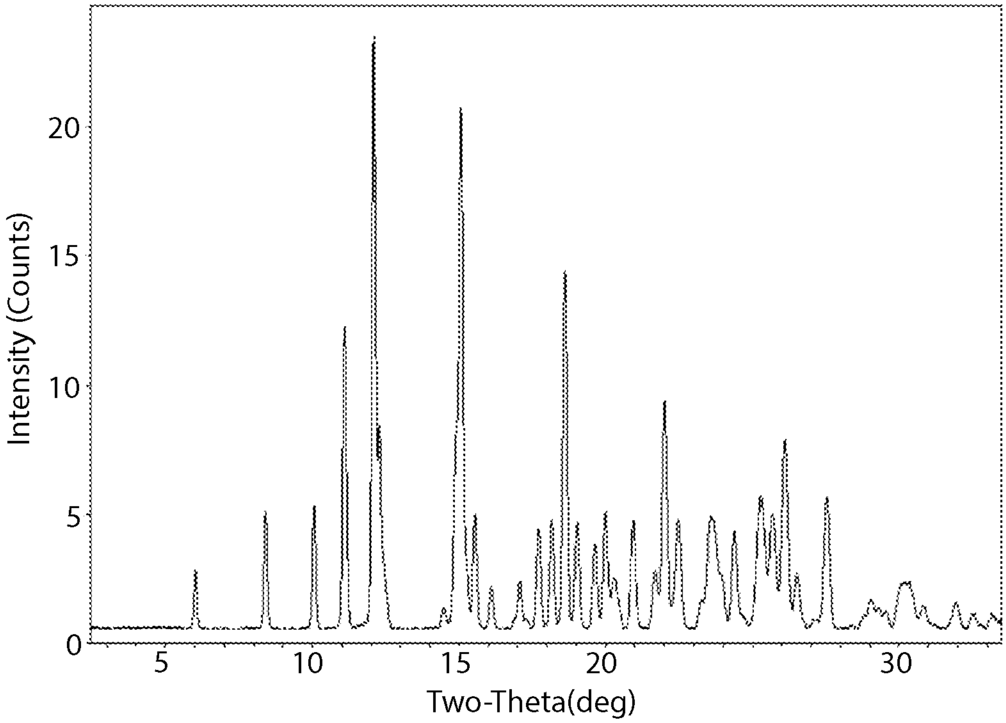
FIG. 1 shows the observed powder x-ray diffraction pattern (CuKα, λ=1.54178 Å at T=25° C.) of crystalline Form A of Compound (I), mono benzenesulfonic acid salt.

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof.

The names used herein to characterize a specific form, e.g., "Form A" etc., are merely identifiers that are to be interpreted in accordance with the characterization information presented herein and are not to be limited so as to exclude any other substance possessing similar or identical physical and chemical characteristics. The name of a specific form should be understood as a mere identifier that should be interpreted according to the characterization information also presented herein.

The definitions set forth herein take precedence over definitions set forth in any patent, patent application, and/or patent application publication incorporated herein by reference.

All numbers expressing quantities of ingredients, weight percentages, temperatures, and so forth that are preceded by the word "about" are to be understood as only approximations so that slight variations above and below the stated number may be used to achieve substantially the same results as the stated number. Accordingly, unless indicated to the contrary, numerical parameters preceded by the word "about" are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

All measurements are subject to experimental error and are within the spirit of the invention.

As used herein, "polymorphs" refer to crystalline forms having the same chemical structure but different spatial arrangements of the molecules and/or ions forming the crystals.

As used herein, "amorphous" refers to a solid form of a molecule and/or ion that is not crystalline. An amorphous solid does not display a definitive X-ray diffraction pattern with sharp maxima.

As used herein, "substantially pure," when used in reference to a crystalline form, means a compound having a purity greater than 90 weight %, including greater than 90, 91, 92, 93, 94, 95, 96, 97, 98, and 99 weight %, and also including equal to about 100 weight % of Compound (I), based on the weight of the compound. The remaining material comprises other form(s) of the compound, and/or reaction impurities and/or processing impurities arising from its preparation. For example, a crystalline form of Compound (I) may be deemed substantially pure in that it has a purity greater than 90 weight %, as measured by means that are at this time known and generally accepted in the art, where the remaining less than 10 weight % of material comprises amorphous and/or other form(s) of Compound (I) and/or reaction impurities and/or processing impurities.

As used herein, a powder x-ray diffraction (PXRD) pattern "comprising" a number of peaks selected from a specified group of peaks, is intended to include PXRD patterns having additional peaks that are not included in the specified group of peaks. For example, a PXRD pattern comprising four or more, preferably five or more, 2θ values selected from: A, B, C, D, E, F, G, and H, is intended to include a PXRD pattern having: (a) four or more, preferably five or more, 2θ values selected from: A, B, C, D, E, F, G, and H; and (b) zero or more peaks that are not one of peaks A, B, C, D, E, F, G, and H.

The presence of reaction impurities and/or processing impurities may be determined by analytical techniques known in the art, such as, for example, chromatography, nuclear magnetic resonance spectroscopy, mass spectrometry, and/or infrared spectroscopy.

As used herein, the unit cell parameter "molecules per unit cell" refers to the number of molecules of Compound (I) in the unit cell.

Benzenesulfonic acid has the structure:

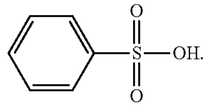

The conjugate base of benzenesulfonic acid is benzenesulfonate. Benzenesulfonic acid salts are also referred to as besylate salts. As used herein, the terms "benzenesulfonic acid salt" and "besylic acid salt" are interchangeable. As used herein, the terms "benzenesulfonate" and "besylate" are interchangeable.

One embodiment provides a benzenesulfonic acid salt of Compound (I) having a stoichiometry of 1:1 and is referred to herein as "mono benzenesulfonic acid salt of Compound (I), "Compound (I), mono benzenesulfonate", "mono besylic acid salt of Compound (I)", or "Compound (I), mono besylate".

In one embodiment, the mono benzenesulfonate salt of Compound (I) is provided as a hydrate.

In one embodiment, the mono benzenesulfonate salt of Compound (I) is provided as a solvate.

In one embodiment, the mono benzenesulfonate salt of Compound (I) is provided as an anhydrate.

In one embodiment, the mono benzenesulfonate salt of Compound (I) is provided as a crystalline material.

In one embodiment, the mono benzenesulfonate salt of Compound (I) is provided as a neat crystalline material.

In one embodiment, the mono benzenesulfonate salt of Compound (I) is provided as a crystalline anhydrate material.

In one embodiment, the mono benzenesulfonate salt of Compound (I) is provided as a crystalline hydrate material.

In one embodiment, the mono benzenesulfonate salt of Compound (I) is provided as a crystalline solvate material.

One embodiment provides a hydrobromic acid salt of Compound (I) having a stoichiometry of 1:1 (Compound (I):HBr) and is referred to herein as "mono hydrobromic acid salt of Compound (I) or "Compound (I), mono hydrobromic acid".

In one embodiment, the mono hydrobromic acid salt of Compound (I) is provided as a crystalline material.

In one embodiment, the mono hydrobromic acid salt of Compound (I) is provided as a neat crystalline material.

In one embodiment, the mono hydrobromic acid salt of Compound (I) is provided as a crystalline anhydrate material.

One embodiment provides a citric acid salt of Compound (I) having a stoichiometry of 1:1 and is referred to herein as "mono citric acid salt of Compound (I) or "Compound (I), mono citrate".

In one embodiment, the mono citric acid salt of Compound (I) is provided as an anhydrate.

In one embodiment, the mono citric acid salt of Compound (I) is provided as a crystalline material.

In one embodiment, the mono citric acid salt of Compound (I) is provided as a neat crystalline material.

In one embodiment, the mono citric acid salt of Compound (I) is provided as a crystalline anhydrate material.

One embodiment provides a hydrochloric acid salt of Compound (I) having a stoichiometry of 1:1 and is referred to herein as "mono hydrochloric acid salt of Compound (I) or "Compound (I), mono hydrochloric acid".

In one embodiment, the mono hydrochloric acid salt of Compound (I) is provided as an anhydrate.

In one embodiment, the mono hydrochloric acid salt of Compound (I) is provided as a crystalline material.

In one embodiment, the mono hydrochloric acid salt of Compound (I) is provided as a neat crystalline material.

In one embodiment, the mono hydrochloric acid salt of Compound (I) is provided as a crystalline anhydrate material.

One embodiment provides a methane sulfonic acid salt of Compound (I) having a stoichiometry of 1:1 and is referred to herein as "mono methane sulfonic acid salt of Compound (I) or "Compound (I), mono methane sulfonate".

In one embodiment, the mono methane sulfonic acid salt of Compound (I) is provided as an anhydrate.

In one embodiment, the mono methane sulfonic acid salt of Compound (I) is provided as a crystalline material.

In one embodiment, the mono methane sulfonic acid salt of Compound (I) is provided as a neat crystalline material.

In one embodiment, the mono methane sulfonic acid salt of Compound (I) is provided as a crystalline anhydrate material.

Form A of Compound (I), Mono Benzenesulfonate

In one embodiment, the mono benzenesulfonic acid salt of Compound (I) is provided as a crystalline material comprising crystalline Form A. The crystalline Form A of Compound (I), benzenesulfonic acid salt has a stoichiometry of 1:1 Compound (I) to benzenesulfonic acid. Crystalline Form A is a non-stoichiometric hydrate. Crystalline Form A is also referred to herein as "Form A".

TABLE 1

Form A of Compound (I), Mono Benzenesulfonate Selected PXRD 2θ values (CuKα λ = 1.5418 Å) measured at room temperature

| | | | | | | |
|---|---|---|---|---|---|---|
| 6.1 ± 0.2 | 8.4 ± 0.2 | 10.1 ± 0.2 | 11.1 ± 0.2 | 12.1 ± 0.2 | 14.5 ± 0.2 | 15.1 ± 0.2 |
| 15.6 ± 0.2 | 16.1 ± 0.2 | 17.1 ± 0.2 | 17.8 ± 0.2 | 18.2 ± 0.2 | 18.7 ± 0.2 | 19.1 ± 0.2 |
| 19.7 ± 0.2 | 20.0 ± 0.2 | 20.4 ± 0.2 | 21.0 ± 0.2 | 21.7 ± 0.2 | 22.0 ± 0.2 | 22.5 ± 0.2 |
| 23.6 ± 0.2 | 24.4 ± 0.2 | 25.3 ± 0.2 | 25.7 ± 0.2 | 26.1 ± 0.2 | 26.6 ± 0.2 | 27.6 ± 0.2 |

In one embodiment, the mono hydrobromic acid salt of Compound (I) is provided as an anhydrate.

In one embodiment, crystalline Form A of Compound (I), mono benzenesulfonate is characterized by a powder x-ray diffraction pattern comprising four or more 2θ values (CuKα λ=1.5418 Å) selected from: 6.1±0.2, 8.4±0.2, 10.1±0.2, 11.1±0.2, 12.1±0.2, 15.1±0.2, 15.6±0.2, 17.8±0.2, 18.2±0.2, and 18.7±0.2, wherein the PXRD pattern of crystalline Form A is measured at a temperature of about 25° C.

In one embodiment, crystalline Form A of Compound (I), mono benzenesulfonate is characterized by a powder x-ray diffraction pattern comprising five or more 2θ values (CuKα λ=1.5418 Å) selected from: 6.1±0.2, 8.4±0.2, 10.1±0.2, 11.1±0.2, 12.1±0.2, 15.1±0.2, 15.6±0.2, 17.8±0.2, 18.2±0.2, and 18.7±0.2, wherein the PXRD pattern of crystalline Form A is measured at a temperature of about 25° C.

In one embodiment, crystalline Form A of Compound (I), mono benzenesulfonate is characterized by a powder x-ray diffraction pattern comprising six or more 2θ values (CuKα λ=1.5418 Å) selected from: 6.1±0.2, 8.4±0.2, 10.1±0.2, 11.1±0.2, 12.1±0.2, 15.1±0.2, 15.6±0.2, 17.8±0.2, 18.2±0.2, and 18.7±0.2, wherein the PXRD pattern of crystalline Form A is measured at a temperature of about 25° C.

In one embodiment, crystalline Form A of Compound (I), mono benzenesulfonate is characterized by an observed powder x-ray diffraction pattern substantially as shown in FIG. 1.

In one embodiment, crystalline Form A of Compound (I), mono benzenesulfonate is characterized by an endotherm in the range of from 292° C. to 296° C.

In one embodiment, crystalline Form A of Compound (I), mono benzenesulfonate is characterized by a thermogravimetric analysis (TGA) thermogram having weight loss of about 5.5 wt % based on the weight of the sample of crystalline Form A, upon being heated to a temperature of about 150° C.

Figure 3:
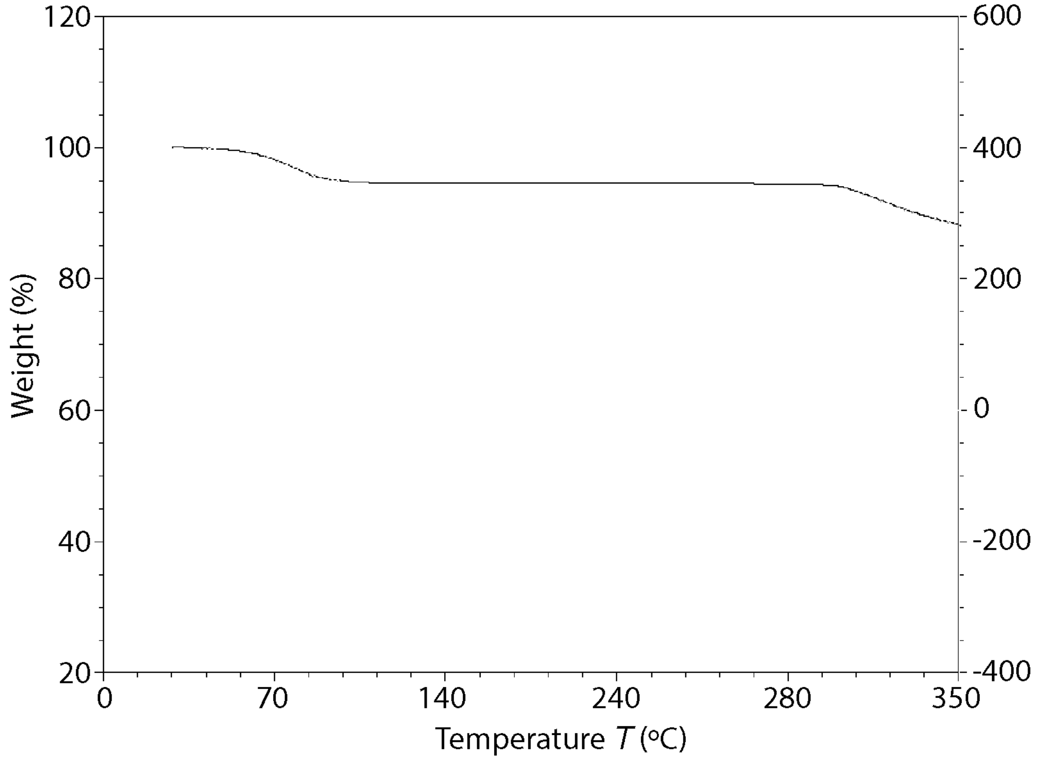
FIG. 3 shows a thermogravimetric analysis (TGA) thermogram of the crystalline Form A of Compound (I), mono benzenesulfonic acid salt.

In one embodiment, crystalline Form A of Compound (I), mono benzenesulfonate exhibits a thermogravimetric analysis (TGA) thermogram substantially as shown in FIG. 3.

Figure 4:
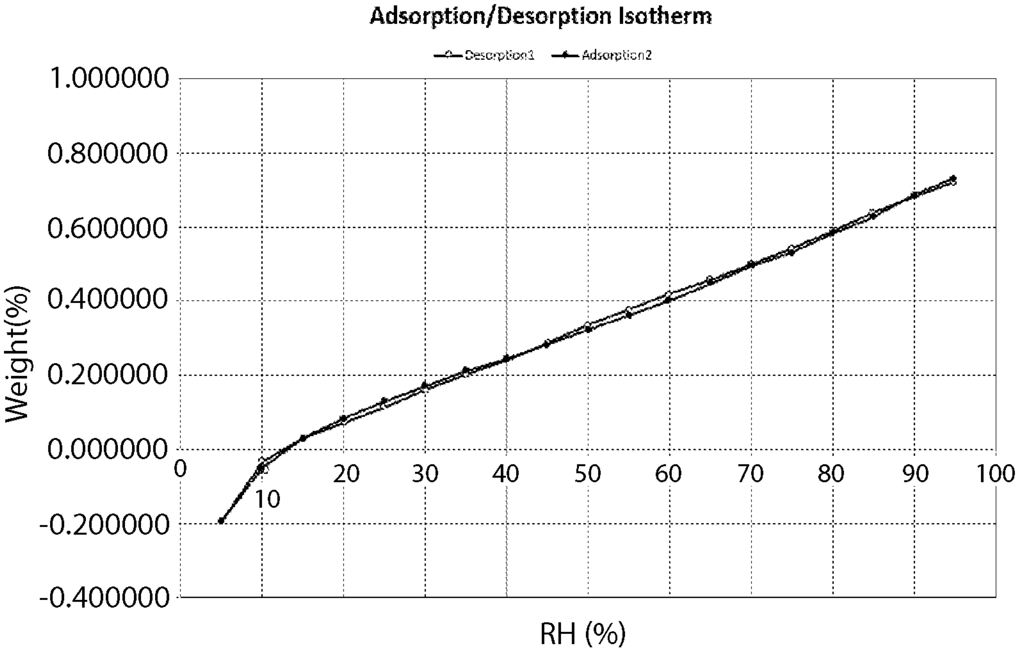
FIG. 4 shows a moisture-sorption isotherm for crystalline Form A of Compound (I), mono benzenesulfonic acid salt at a temperature of 25° C.

In one embodiment, crystalline Form A of Compound (I), mono benzenesulfonate exhibits a moisture-sorption isotherm substantially as shown in FIG. 4.

Figure 5:
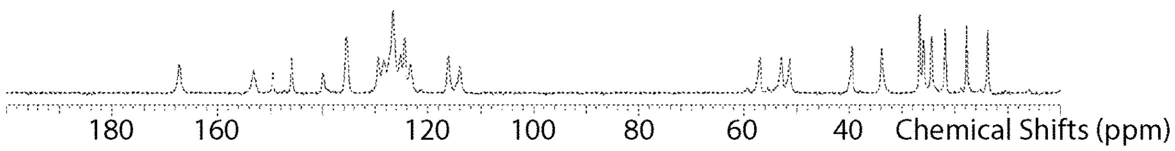
FIG. 5 shows the $^{13}C$-$^{1}H$ CPMAS solid state NMR spectrum of crystalline Form A of Compound (I), mono benzenesulfonic acid salt at a temperature of 280 K.

In one embodiment, crystalline Form A of Compound (I), mono benzenesulfonate exhibits a $^{13}C$-$^{1}H$ CPMAS solid state NMR spectrum substantially as shown in FIG. 5.

In one embodiment, crystalline Form A of Compound (I), mono benzenesulfonate has a stoichiometry of about 1.6 to about 2.3 water molecules for each molecule of Compound (I).

In one embodiment, crystalline Form A of Compound (I), mono benzenesulfonate has a stoichiometry of about 1.7 to about 2.2 water molecules for each molecule of Compound (I).

In one embodiment, crystalline Form A of Compound (I), mono benzenesulfonate has a stoichiometry of about 1.8 to about 2.1 water molecules for each molecule of Compound (I).

TABLE 2

Form A of Compound (I), mono benzenesulfonate salt Observed $^{13}C$ Solid State NMR Peaks measured at 280 K (ppm)

| | | | | | |
|---|---|---|---|---|---|
| 13.7 ± 0.2 | 17.7 ± 0.2 | 21.8 ± 0.2 | 24.4 ± 0.2 | 26.0 ± 0.2 | 26.7 ± 0.2 |
| 33.8 ± 0.2 | 39.6 ± 0.2 | 51.4 ± 0.2 | 53.0 ± 0.2 | 57.1 ± 0.2 | 114.0 ± 0.2 |
| 116.2 ± 0.2 | 123.4 ± 0.2 | 125.2 ± 0.2 | 126.7 ± 0.2 | 128.4 ± 0.2 | 129.4 ± 0.2 |
| 135.6 ± 0.2 | 139.9 ± 0.2 | 145.8 ± 0.2 | 149.4 ± 0.2 | 153.2 ± 0.2 | 167.2 ± 0.2 |

In one embodiment, crystalline Form A of Compound (I), mono benzenesulfonate is characterized by a $^{13}C$ solid state NMR spectrum comprising six or more peaks selected from 13.7±0.2, 17.7±0.2, 21.8±0.2, 24.4±0.2, 26.0±0.2, 26.7±0.2, 33.8±0.2, 39.6±0.2, 51.4±0.2, 53.0±0.2, 57.1±0.2, 114.0±0.2, 116.2±0.2, 123.4±0.2, 125.2±0.2, 126.7±0.2, 128.4±0.2, 129.4±0.2, 135.6±0.2, 139.9±0.2, 145.8±0.2, 149.4±0.2, 153.2±0.2, and 167.2±0.2 ppm, wherein the $^{13}C$ solid state NMR spectrum of crystalline Form A is measured at a temperature of about 280 K.

Figure 2:
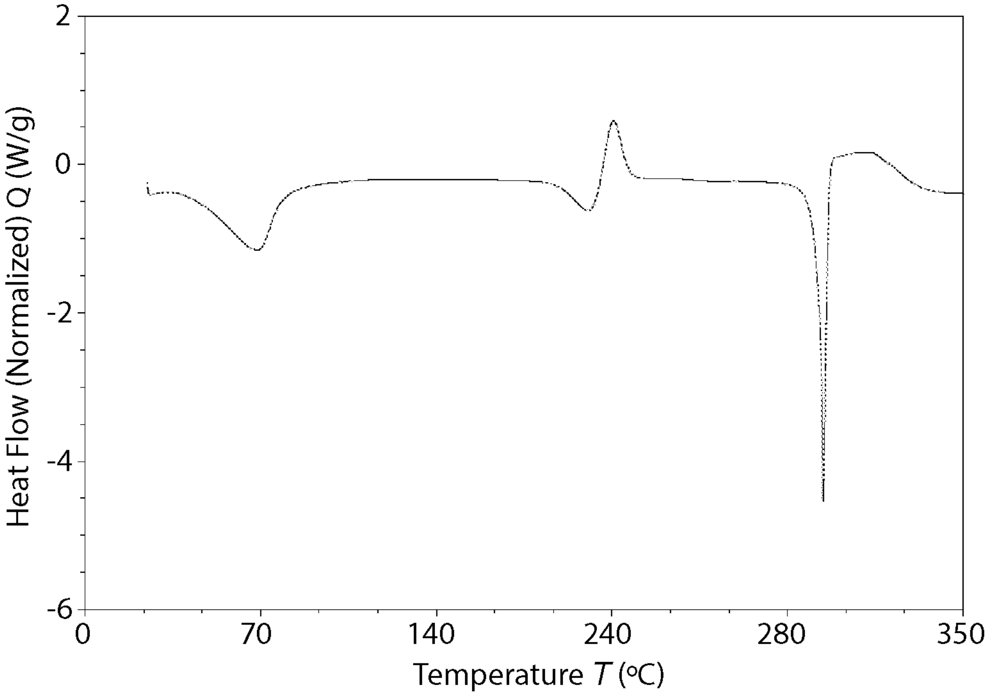
FIG. 2 shows a differential scanning calorimetry (DSC) thermogram of crystalline Form A of Compound (I), mono benzenesulfonic acid salt.

In one embodiment, crystalline Form A of Compound (I), mono benzenesulfonate salt, is characterized by a differential scanning calorimetry (DSC) thermogram substantially as shown in FIG. 2.

In one embodiment, crystalline Form A of Compound (I), mono benzenesulfonate is characterized by (i) a powder x-ray diffraction pattern comprising the 2θ values (CuKα λ=1.5418 Å) at 12.1±0.2 and 15.1±0.2, measured at a temperature of about 25° C.; and (ii) a differential scanning calorimetry (DSC) thermogram substantially in accordance with that shown in FIG. 2.

In one embodiment, crystalline Form A of Compound (I), mono benzenesulfonate is characterized by (i) a powder x-ray diffraction pattern comprising four or more 2θ values (CuKα λ=1.5418 Å) selected from: 6.1±0.2, 8.4±0.2, 10.1±0.2, 11.1±0.2, 12.1±0.2, 15.1±0.2, 15.6±0.2, 17.8±0.2, 18.2±0.2, and 18.7±0.2, wherein the PXRD pattern of crystalline Form A is measured at a temperature of about 25° C.; and (ii) a melting point in the range of from 292° C. to 296° C.

In one embodiment, crystalline Form A of Compound (I), mono benzenesulfonate is a dihydrate.

In one embodiment, crystalline Form A of Compound (I), mono benzenesulfonate has from 4.5 to 6.5 weight % water.

In one embodiment, crystalline Form A of Compound (I), mono benzenesulfonate has from 4.8 to 6.2 weight % water.

In one embodiment, crystalline Form A of Compound (I), mono benzenesulfonate has from 5.0 to 6.0 weight % water.

In one embodiment, crystalline Form A of Compound (I), mono benzenesulfonate has from 5.2 to 5.9 weight % water.

In still yet an even further embodiment, crystalline Form A of Compound (I), mono benzenesulfonate is substantially pure.

In another embodiment, the crystalline form of Compound (I), mono benzenesulfonate consists essentially of crystalline Form A. The crystalline form of this embodiment may comprise at least about 90 wt. %, preferably at least about 95 wt. %, and more preferably at least about 99 wt. %, based on the weight of the crystalline form, crystalline Form A of Compound (I), mono benzenesulfonate salt.

One embodiment provides a composition comprising 2-(4-(2-(7,8-dimethyl-[1,2,4]triazolo[1,5-a]pyridin-6-yl)-3-isopropyl-1H-indol-5-yl) piperidin-1-yl)acetamide, mono benzenesulfonate salt, wherein at least 95 wt. 00 preferably at least 97 wt. %, and more preferably at least 99 wt. % of said 2-(4-(2-(7,8-dimethyl-[1,2,4]triazolo[1,5-a]pyridin-6-yl)-3-isopropyl-1H-indol-5-yl) piperidin-1-yl)acetamide, mono benzenesulfonate is in crystalline Form A.

Form C of Compound (I), Mono Benzenesulfonate Solvate

In one embodiment, the mono benzenesulfonic acid salt of Compound (I) is provided as a crystalline material comprising Form C. The crystalline Form C of Compound (I), benzenesulfonic acid salt has a stoichiometry of 1:1 Compound (I) to benzenesulfonic acid. Crystalline Form C is a solvate comprising acetone, acetonitrile, dichloromethane, dimethyl formamide, dimethylsulfoxide, isopropanol, isopropyl acetate, methyl isobutyl ketone, or tetrahydrofuran. Crystalline Form C is also referred to herein as "Form C".

TABLE 3

Form C of Compound (I), Mono Benzenesulfonate Tetrahydrofuran Solvate Selected PXRD 2θ values (CuKα λ = 1.5418 Å) measured at room temperature

| | | | | | |
|---|---|---|---|---|---|
| 5.1 ± 0.2 | 7.7 ± 0.2 | 8.1 ± 0.2 | 10.2 ± 0.2 | 10.7 ± 0.2 | 11.2 ± 0.2 |
| 11.6 ± 0.2 | 12.9 ± 0.2 | 13.2 ± 0.2 | 13.5 ± 0.2 | 14.1 ± 0.2 | 14.6 ± 0.2 |
| 15.0 ± 0.2 | 15.3 ± 0.2 | 15.9 ± 0.2 | 16.5 ± 0.2 | 16.9 ± 0.2 | 17.6 ± 0.2 |
| 18.2 ± 0.2 | 18.6 ± 0.2 | 19.3 ± 0.2 | 20.2 ± 0.2 | 20.5 ± 0.2 | 21.0 ± 0.2 |
| 21.5 ± 0.2 | 22.6 ± 0.2 | 23.1 ± 0.2 | 24.2 ± 0.2 | 24.8 ± 0.2 | 25.5 ± 0.2 |
| 25.8 ± 0.2 | 26.0 ± 0.2 | 26.7 ± 0.2 | 27.1 ± 0.2 | 29.2 ± 0.2 | 29.5 ± 0.2 |
| 30.1 ± 0.2 | 30.6 ± 0.2 | 30.9 ± 0.2 | 31.9 ± 0.2 | — | — |

In one embodiment, crystalline Form C of Compound (I), mono benzenesulfonate is characterized by a powder x-ray diffraction pattern comprising four or more 2θ values (CuKα λ=1.5418 Å) selected from: 5.1±0.2, 7.7±0.2, 8.1±0.2, 10.2±0.2, 11.2±0.2, 11.6±0.2, 12.9±0.2, 14.1±0.2, 14.6±0.2, 15.0±0.2, 18.6±0.2, 19.3±0.2, 21.5±0.2, 23.1±0.2, and 24.8±0.2, wherein the PXRD pattern of crystalline Form C is measured at a temperature of about 25° C.

In one embodiment, crystalline Form C of Compound (I), mono benzenesulfonate is characterized by a powder x-ray diffraction pattern comprising five or more 2θ values (CuKα λ=1.5418 Å) selected from: 5.1±0.2, 7.7±0.2, 8.1±0.2, 10.2±0.2, 11.2±0.2, 11.6±0.2, 12.9±0.2, 14.1±0.2, 14.6±0.2, 15.0±0.2, 18.6±0.2, 19.3±0.2, 21.5±0.2, 23.1±0.2, and 24.8±0.2, wherein the PXRD pattern of crystalline Form C is measured at a temperature of about 25° C.

In one embodiment, crystalline Form C of Compound (I), mono benzenesulfonate is characterized by a powder x-ray diffraction pattern comprising six or more 2θ values (CuKα λ=1.5418 Å) selected from: 5.1±0.2, 7.7±0.2, 8.1±0.2, 10.2±0.2, 11.2±0.2, 11.6±0.2, 12.9±0.2, 14.1±0.2, 14.6±0.2, 15.0±0.2, 18.6±0.2, 19.3±0.2, 21.5±0.2, 23.1±0.2, and 24.8±0.2, wherein the PXRD pattern of crystalline Form C is measured at a temperature of about 25° C.

Figure 6:
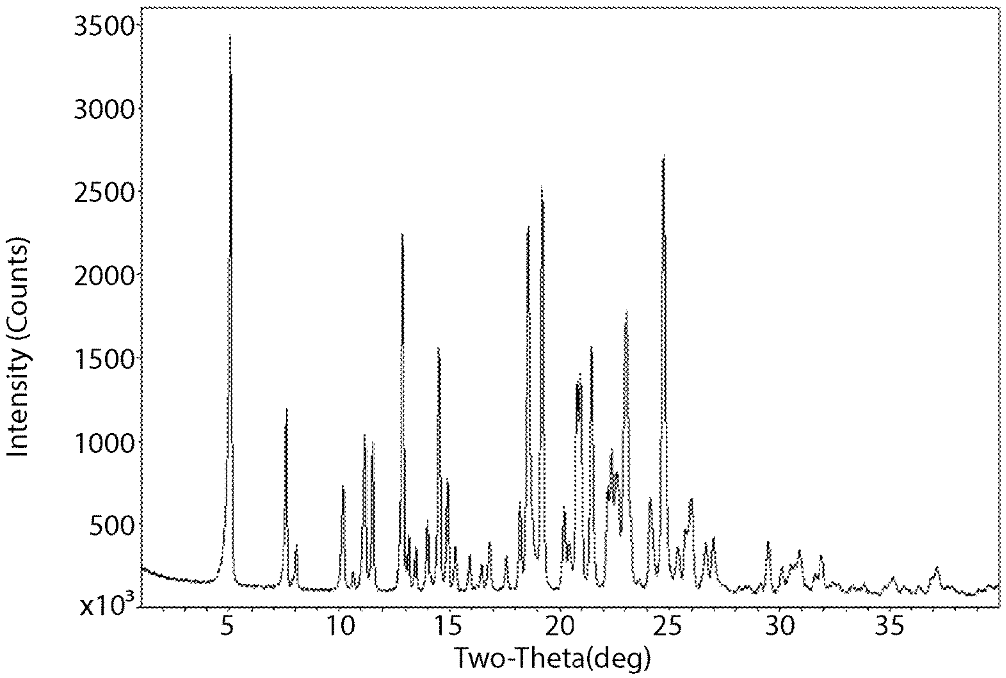
FIG. 6 shows the observed powder x-ray diffraction pattern (CuKα, λ=1.54178 Å at T=25° C.) of crystalline Form C of Compound (I), mono benzenesulfonic acid salt.

In one embodiment, crystalline Form C of Compound (I), mono benzenesulfonate is characterized by an observed powder x-ray diffraction pattern substantially as shown in FIG. 6.

In one embodiment, crystalline Form C of Compound (I), mono benzenesulfonate has a stoichiometry of about one solvent molecule for each molecule of Compound (I), wherein the solvent is acetone, acetonitrile, dichloromethane, dimethylformamide, dimethylsulfoxide, and tetrahydrofuran.

In one embodiment, crystalline Form C of Compound (I), mono benzenesulfonate has a stoichiometry of about less than one solvent molecule for each molecule of Compound (I), wherein the solvent is isopropanol, isopropyl acetate, and methyl isobutyl ketone.

In still yet an even further embodiment, crystalline Form C of Compound (I), mono benzenesulfonate is substantially pure.

In another embodiment, the crystalline form of Compound (I), mono benzenesulfonate consists essentially of crystalline Form C. The crystalline form of this embodiment may comprise at least about 90 wt. %, preferably at least about 95 wt. %, and more preferably at least about 99 wt. %, based on the weight of the crystalline form, crystalline Form C of Compound (I), mono benzenesulfonate salt.

One embodiment provides a composition comprising 2-(4-(2-(7,8-dimethyl-[1,2,4]triazolo[1,5-a]pyridin-6-yl)-3-isopropyl-1H-indol-5-yl) piperidin-1-yl)acetamide, mono benzenesulfonate salt, wherein at least 95 wt. preferably at least 97 wt. %, and more preferably at least 99 wt. % of said 2-(4-(2-(7,8-dimethyl-[1,2,4]triazolo[1,5-a]pyridin-6-yl)-3-isopropyl-1H-indol-5-yl) piperidin-1-yl)acetamide, mono benzenesulfonate is in crystalline Form C.

Form D of Compound (I), Mono Benzenesulfonate Anhydrate

In one embodiment, the mono benzenesulfonic acid salt of Compound (I) is provided as a crystalline material comprising crystalline Form D. The crystalline Form D of Compound (I), benzenesulfonic acid salt has a stoichiometry of 1:1 Compound (I) to benzenesulfonic acid. Crystalline Form D is an anhydrate. Crystalline Form D is also referred to herein as "Form D".

TABLE 4

Form D of Compound (I), Mono Benzenesulfonate Anhydrate Selected PXRD 2θ values (CuKα λ = 1.5418 A) measured at room temperature

| | | | | | |
|---|---|---|---|---|---|
| 6.1 ± 0.2 | 8.1 ± 0.2 | 10.7 ± 0.2 | 11.5 ± 0.2 | 12.2 ± 0.2 | 12.7 ± 0.2 |
| 13.0 ± 0.2 | 14.8 ± 0.2 | 15.2 ± 0.2 | 15.5 ± 0.2 | 15.8 ± 0.2 | 16.7 ± 0.2 |
| 17.3 ± 0.2 | 17.9 ± 0.2 | 18.7 ± 0.2 | 19.5 ± 0.2 | 20.1 ± 0.2 | 20.5 ± 0.2 |
| 20.6 ± 0.2 | 21.0 ± 0.2 | 21.4 ± 0.2 | 21.7 ± 0.2 | 22.3 ± 0.2 | 22.6 ± 0.2 |
| 23.4 ± 0.2 | 23.8 ± 0.2 | 24.4 ± 0.2 | 24.8 ± 0.2 | 25.1 ± 0.2 | 25.5 ± 0.2 |
| 26.2 ± 0.2 | 26.6 ± 0.2 | 27.1 ± 0.2 | 27.3 ± 0.2 | 27.6 ± 0.2 | 28.0 ± 0.2 |
| 28.4 ± 0.2 | 29.5 ± 0.2 | 30.0 ± 0.2 | 30.9 ± 0.2 | 31.5 ± 0.2 | 31.9 ± 0.2 |
| 32.4 ± 0.2 | 32.7 ± 0.2 | 33.2 ± 0.2 | — | — | — |

In one embodiment, crystalline Form D of Compound (I), mono benzenesulfonate is characterized by a powder x-ray diffraction pattern comprising four or more 2θ values (CuKα λ=1.5418 Å) selected from: 6.1±0.2, 8.1±0.2, 10.7±0.2, 11.7±0.2, 12.2±0.2, 12.7±0.2, 13.0±0.2, 14.8±0.2, 15.5±0.2, 16.7±0.2, 17.9±0.2, and 19.5±0.2, wherein the PXRD pattern of crystalline Form D is measured at a temperature of about 25° C.

In one embodiment, crystalline Form D of Compound (I), mono benzenesulfonate is characterized by a powder x-ray diffraction pattern comprising five or more 2θ values (CuKα λ=1.5418 Å) selected from: 6.1±0.2, 8.1±0.2, 10.7±0.2, 11.7±0.2, 12.2±0.2, 12.7±0.2, 13.0±0.2, 14.8±0.2, 15.5±0.2, 16.7±0.2, 17.9±0.2, and 19.5±0.2, wherein the PXRD pattern of crystalline Form D is measured at a temperature of about 25° C.

In one embodiment, crystalline Form D of Compound (I), mono benzenesulfonate is characterized by a powder x-ray diffraction pattern comprising six or more 2θ values (CuKα λ=1.5418 Å) selected from: 6.1±0.2, 8.1±0.2, 10.7±0.2, 11.7±0.2, 12.2±0.2, 12.7±0.2, 13.0±0.2, 14.8±0.2, 15.5±0.2, 16.7±0.2, 17.9±0.2, and 19.5±0.2, wherein the PXRD pattern of crystalline Form D is measured at a temperature of about 25° C.

Figure 7:
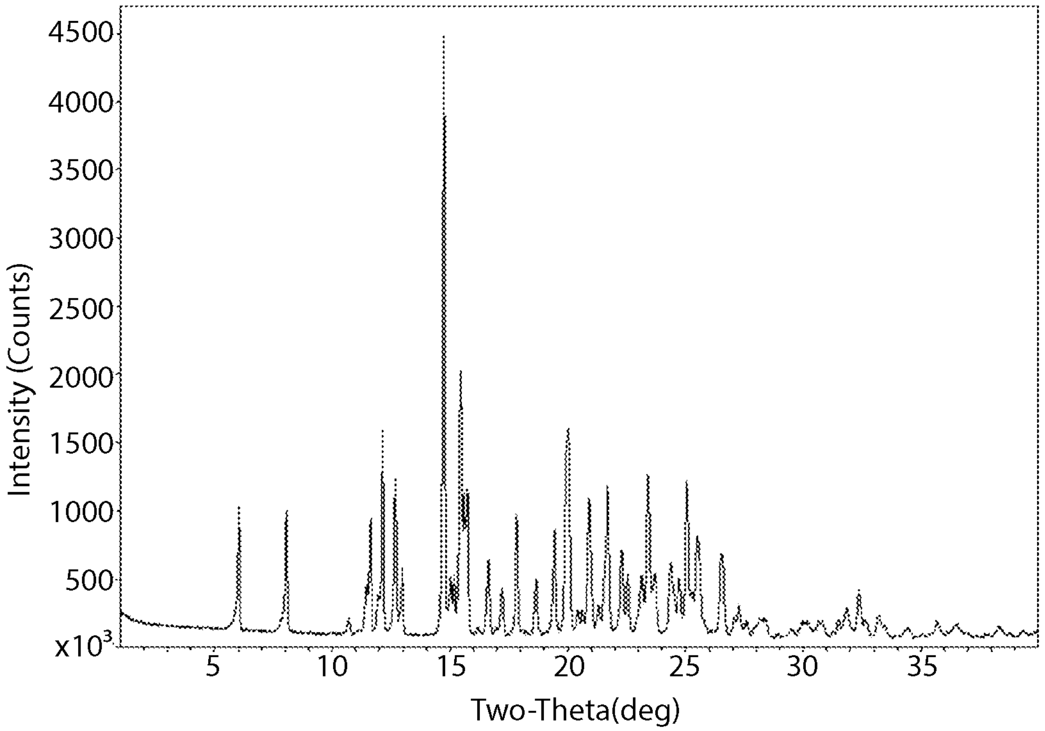
FIG. 7 shows the observed powder x-ray diffraction pattern (CuKα, λ=1.54178 Å at T=25° C.) of crystalline Form D of Compound (I), mono benzenesulfonic acid salt.

In one embodiment, crystalline Form D of Compound (I), mono benzenesulfonate is characterized by an observed powder x-ray diffraction pattern substantially as shown in FIG. 7.

In still yet an even further embodiment, crystalline Form D of Compound (I), mono benzenesulfonate is substantially pure.

In another embodiment, the crystalline form of Compound (I), mono benzenesulfonate consists essentially of crystalline Form D. The crystalline form of this embodiment may comprise at least about 90 wt. %, preferably at least about 95 wt. %, and more preferably at least about 99 wt. %, based on the weight of the crystalline form, crystalline Form D of Compound (I), mono benzenesulfonate salt.

One embodiment provides a composition comprising 2-(4-(2-(7,8-dimethyl-[1,2,4]triazolo[1,5-a]pyridin-6-yl)-3-isopropyl-1H-indol-5-yl) piperidin-1-yl)acetamide, mono benzenesulfonate salt, wherein at least 95 wt. %, preferably at least 97 wt. %, and more preferably at least 99 wt. % of said 2-(4-(2-(7,8-dimethyl-[1,2,4]triazolo[1,5-a]pyridin-6-yl)-3-isopropyl-1H-indol-5-yl) piperidin-1-yl)acetamide, mono benzenesulfonate is in crystalline Form D.

Form E of Compound (I), Mono Benzenesulfonate Anhydrate

In one embodiment, the mono benzenesulfonic acid salt of Compound (I) is provided as a crystalline material comprising crystalline Form E. The crystalline Form E of Compound (I), benzenesulfonic acid salt has a stoichiometry of 1:1 Compound (I) to benzenesulfonic acid. Crystalline Form E is an anhydrate. Crystalline Form E is also referred to herein as "Form E".

TABLE 5

Form E of Compound (I), Mono Benzenesulfonate Anhydrate Selected PXRD 2θ values (CuKα λ = 1.5418 Å) measured at room temperature

| | | | | | |
|---|---|---|---|---|---|
| 5.8 ± 0.2 | 7.1 ± 0.2 | 7.6 ± 0.2 | 8.4 ± 0.2 | 9.8 ± 0.2 | 11.2 ± 0.2 |
| 11.6 ± 0.2 | 12.3 ± 0.2 | 12.7 ± 0.2 | 13.0 ± 0.2 | 13.5 ± 0.2 | 13.9 ± 0.2 |
| 14.2 ± 0.2 | 14.5 ± 0.2 | 15.0 ± 0.2 | 15.9 ± 0.2 | 16.1 ± 0.2 | 16.7 ± 0.2 |
| 16.9 ± 0.2 | 17.8 ± 0.2 | 18.1 ± 0.2 | 18.4 ± 0.2 | 18.9 ± 0.2 | 19.5 ± 0.2 |
| 19.7 ± 0.2 | 20.1 ± 0.2 | 20.6 ± 0.2 | 20.9 ± 0.2 | 21.3 ± 0.2 | 21.7 ± 0.2 |
| 22.5 ± 0.2 | 22.7 ± 0.2 | 22.9 ± 0.2 | 23.5 ± 0.2 | 23.9 ± 0.2 | 24.4 ± 0.2 |
| 24.9 ± 0.2 | 25.2 ± 0.2 | 25.5 ± 0.2 | 25.9 ± 0.2 | 26.2 ± 0.2 | 26.6 ± 0.2 |
| 27.8 ± 0.2 | 28.2 ± 0.2 | 28.6 ± 0.2 | 29.2 ± 0.2 | 29.5 ± 0.2 | 30.6 ± 0.2 |
| 31.3 ± 0.2 | — | — | — | — | — |

In one embodiment, crystalline Form E of Compound (I), mono benzenesulfonate is characterized by a powder x-ray diffraction pattern comprising four or more 2θ values (CuKα λ=1.5418 Å) selected from: 5.8±0.2, 7.1±0.2, 9.8±0.2, 12.3±0.2, 13.5±0.2, 13.9±0.2, 15.9±0.2, 17.8±0.2, 18.1±0.2, 18.9±0.2, and 21.7±0.2, wherein the PXRD pattern of crystalline Form E is measured at a temperature of about 25° C.

In one embodiment, crystalline Form E of Compound (I), mono benzenesulfonate is characterized by a powder x-ray diffraction pattern comprising five or more 2θ values (CuKα λ=1.5418 Å) selected from: 5.8±0.2, 7.1±0.2, 9.8±0.2, 12.3±0.2, 13.5±0.2, 13.9±0.2, 15.9±0.2, 17.8±0.2, 18.1±0.2, 18.9±0.2, and 21.7±0.2, wherein the PXRD pattern of crystalline Form E is measured at a temperature of about 25° C.

In one embodiment, crystalline Form E of Compound (I), mono benzenesulfonate is characterized by a powder x-ray diffraction pattern comprising six or more 2θ values (CuKα λ=1.5418 Å) selected from: 5.8±0.2, 7.1±0.2, 9.8±0.2, 12.3±0.2, 13.5±0.2, 13.9±0.2, 15.9±0.2, 17.8±0.2, 18.1±0.2, 18.9±0.2, and 21.7±0.2, wherein the PXRD pattern of crystalline Form E is measured at a temperature of about 25° C.

Figure 8:
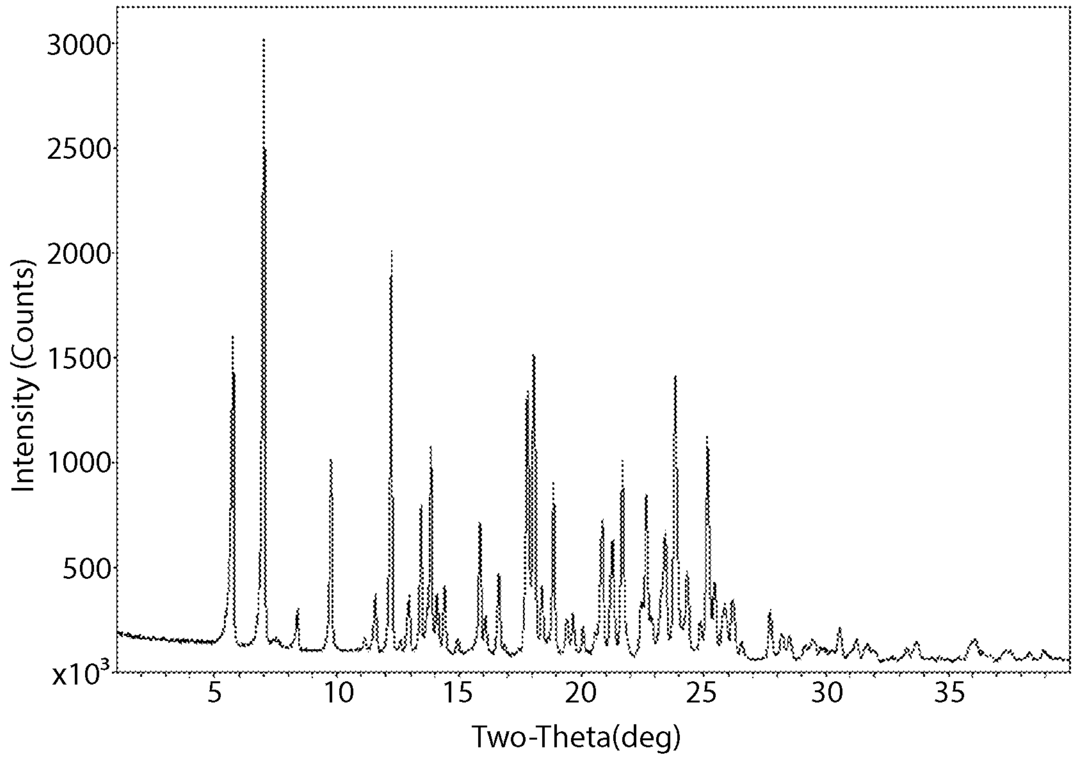
FIG. 8 shows the observed powder x-ray diffraction pattern (CuKα, λ=1.54178 Å at T=25° C.) of crystalline Form E of Compound (I), mono benzenesulfonic acid salt.

In one embodiment, crystalline Form E of Compound (I), mono benzenesulfonate is characterized by an observed powder x-ray diffraction pattern substantially as shown in FIG. 8.

In still yet an even further embodiment, crystalline Form E of Compound (I), mono benzenesulfonate is substantially pure.

In another embodiment, the crystalline form of Compound (I), mono benzenesulfonate consists essentially of crystalline Form E. The crystalline form of this embodiment may comprise at least about 90 wt. %, preferably at least about 95 wt. %, and more preferably at least about 99 wt. %, based on the weight of the crystalline form, crystalline Form E of Compound (I), mono benzenesulfonate salt.

One embodiment provides a composition comprising 2-(4-(2-(7,8-dimethyl-[1,2,4]triazolo[1,5-a]pyridin-6-yl)-3-isopropyl-1H-indol-5-yl) piperidin-1-yl)acetamide, mono benzenesulfonate salt, wherein at least 95 wt. 00 preferably at least 97 wt. %, and more preferably at least 99 wt. % of said 2-(4-(2-(7,8-dimethyl-[1,2,4]triazolo[1,5-a]pyridin-6-yl)-3-isopropyl-1H-indol-5-yl) piperidin-1-yl)acetamide, mono benzenesulfonate is in crystalline Form E.

Form F of Compound (I), Mono Benzenesulfonate Anhydrate

In one embodiment, the mono benzenesulfonic acid salt of Compound (I) is provided as a crystalline material comprising crystalline Form F. The crystalline Form F of Compound (I), benzenesulfonic acid salt has a stoichiometry of 1:1 Compound (I) to benzenesulfonic acid. Crystalline Form F is an anhydrate. Crystalline Form F is also referred to herein as "Form F".

TABLE 6

Form F of Compound (I), Mono Benzenesulfonate Anhydrate Selected PXRD 2θ values (CuKα λ = 1.5418 Å) measured at room temperature

| | | | | | |
|---|---|---|---|---|---|
| 5.6 ± 0.2 | 7.4 ± 0.2 | 8.4 ± 0.2 | 10.3 ± 0.2 | 11.3 ± 0.2 | 12.1 ± 0.2 |
| 13.1 ± 0.2 | 13.6 ± 0.2 | 14.9 ± 0.2 | 15.6 ± 0.2 | 16.3 ± 0.2 | 17.2 ± 0.2 |
| 18.4 ± 0.2 | 20.0 ± 0.2 | 20.3 ± 0.2 | 21.5 ± 0.2 | 22.0 ± 0.2 | 22.3 ± 0.2 |
| 22.9 ± 0.2 | 23.9 ± 0.2 | 24.5 ± 0.2 | 25.0 ± 0.2 | 25.4 ± 0.2 | 26.3 ± 0.2 |
| 27.7 ± 0.2 | 28.7 ± 0.2 | 29.5 ± 0.2 | 30.0 ± 0.2 | 30.7 ± 0.2 | 31.4 ± 0.2 |
| 31.7 ± 0.2 | 33.1 ± 0.2 | — | — | — | — |

In one embodiment, crystalline Form F of Compound (I), mono benzenesulfonate is characterized by a powder x-ray diffraction pattern comprising four or more 2θ values (CuKα λ=1.5418 Å) selected from: 5.6±0.2, 7.4±0.2, 8.4±0.2, 10.3±0.2, 11.3±0.2, 12.1±0.2, 13.1±0.2, 13.6±0.2, 15.6±0.2, 18.4±0.2, 22.9±0.2, and 24.5±0.2, wherein the PXRD pattern of crystalline Form F is measured at a temperature of about 25° C.

In one embodiment, crystalline Form F of Compound (I), mono benzenesulfonate is characterized by a powder x-ray diffraction pattern comprising five or more 2θ values (CuKα λ=1.5418 Å) selected from: 5.6±0.2, 7.4±0.2, 8.4±0.2, 10.3±0.2, 11.3±0.2, 12.1±0.2, 13.1±0.2, 13.6±0.2, 15.6±0.2, 18.4±0.2, 22.9±0.2, and 24.5±0.2, wherein the PXRD pattern of crystalline Form F is measured at a temperature of about 25° C.

In one embodiment, crystalline Form F of Compound (I), mono benzenesulfonate is characterized by a powder x-ray diffraction pattern comprising six or more 2θ values (CuKα λ=1.5418 Å) selected from: 5.6±0.2, 7.4±0.2, 8.4±0.2, 10.3±0.2, 11.3±0.2, 12.1±0.2, 13.1±0.2, 13.6±0.2, 15.6±0.2, 18.4±0.2, 22.9±0.2, and 24.5±0.2, wherein the PXRD pattern of crystalline Form F is measured at a temperature of about 25° C.

Figure 9:
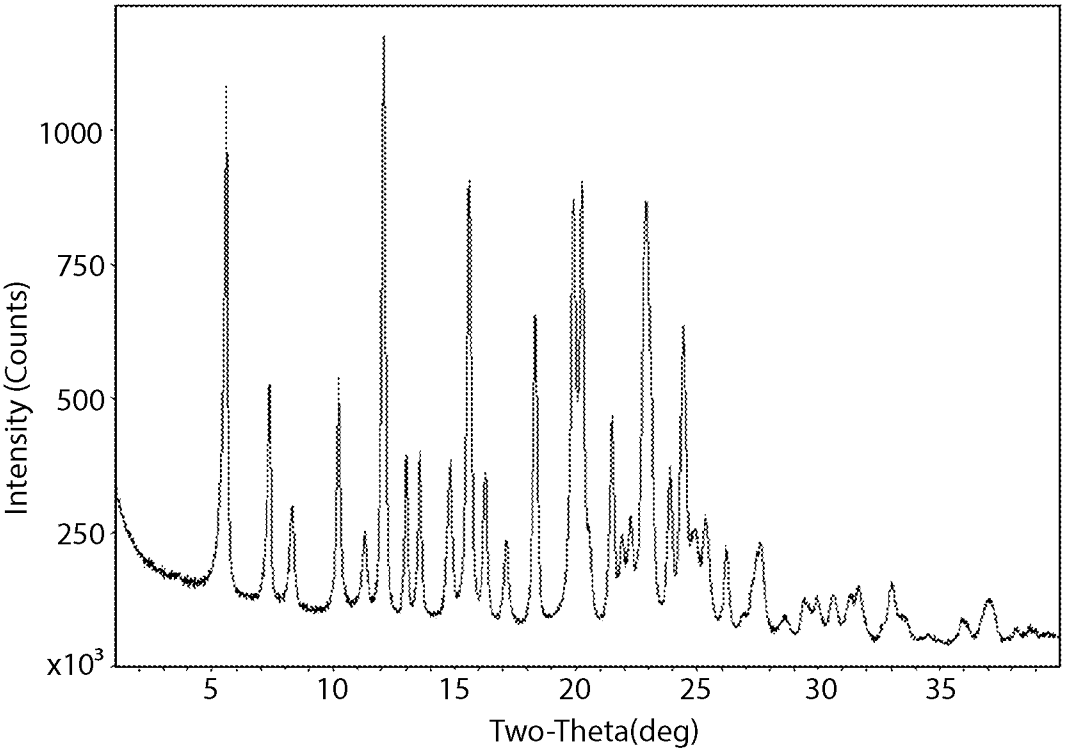
FIG. 9 shows the observed powder x-ray diffraction pattern (CuKα, λ=1.54178 Å at T=25° C.) of crystalline Form F of Compound (I), mono benzenesulfonic acid salt.

In one embodiment, crystalline Form F of Compound (I), mono benzenesulfonate is characterized by an observed powder x-ray diffraction pattern substantially as shown in FIG. 9.

In still yet an even further embodiment, crystalline Form F of Compound (I), mono benzenesulfonate is substantially pure.

In another embodiment, the crystalline form of Compound (I), mono benzenesulfonate consists essentially of crystalline Form F. The crystalline form of this embodiment may comprise at least about 90 wt. %, preferably at least about 95 wt. %, and more preferably at least about 99 wt. %, based on the weight of the crystalline form, crystalline Form F of Compound (I), mono benzenesulfonate salt.

One embodiment provides a composition comprising 2-(4-(2-(7,8-dimethyl-[1,2,4]triazolo[1,5-a]pyridin-6-yl)-3-isopropyl-1H-indol-5-yl) piperidin-1-yl)acetamide, mono benzenesulfonate salt, wherein at least 95 wt. 00 preferably at least 97 wt. %, and more preferably at least 99 wt. % of said 2-(4-(2-(7,8-dimethyl-[1,2,4]triazolo[1,5-a]pyridin-6-yl)-3-isopropyl-1H-indol-5-yl) piperidin-1-yl)acetamide, mono benzenesulfonate is in crystalline Form F.

Form G of Compound (I), Mono Benzenesulfonate Anhydrate

In one embodiment, the mono benzenesulfonic acid salt of Compound (I) is provided as a crystalline material comprising crystalline Form G. The crystalline Form G of Compound (I), benzenesulfonic acid salt has a stoichiometry of 1:1 Compound (I) to benzenesulfonic acid. Crystalline Form G is an anhydrate. Crystalline Form G is also referred to herein as "Form G".

TABLE 7

Form G of Compound (I), Mono Benzenesulfonate Anhydrate Selected PXRD 2θ values (CuKα λ = 1.5418 Å) measured at room temperature

| | | | | | |
|---|---|---|---|---|---|
| 3.3 ± 0.2 | 6.2 ± 0.2 | 6.6 ± 0.2 | 7.9 ± 0.2 | 9.3 ± 0.2 | 9.9 ± 0.2 |
| 10.8 ± 0.2 | 11.4 ± 0.2 | 12.0 ± 0.2 | 12.5 ± 0.2 | 12.8 ± 0.2 | 13.4 ± 0.2 |
| 14.0 ± 0.2 | 15.0 ± 0.2 | 15.5 ± 0.2 | 15.8 ± 0.2 | 16.1 ± 0.2 | 16.5 ± 0.2 |
| 17.2 ± 0.2 | 18.1 ± 0.2 | 18.6 ± 0.2 | 19.4 ± 0.2 | 20.4 ± 0.2 | 20.7 ± 0.2 |
| 21.7 ± 0.2 | 22.1 ± 0.2 | 22.4 ± 0.2 | 23.0 ± 0.2 | 23.6 ± 0.2 | 24.2 ± 0.2 |
| 24.9 ± 0.2 | 26.1 ± 0.2 | 26.7 ± 0.2 | 28.0 ± 0.2 | 30.0 ± 0.2 | 34.7 ± 0.2 |
| 35.5 ± 0.2 | 37.7 ± 0.2 | — | — | — | — |

In one embodiment, crystalline Form G of Compound (I), mono benzenesulfonate is characterized by a powder x-ray diffraction pattern comprising four or more 2θ values (CuKα λ=1.5418 Å) selected from: 3.3±0.2, 6.2±0.2, 6.6±0.2, 7.9±0.2, 9.3±0.2, 9.9±0.2, 12.0±0.2, 12.5±0.2, 12.8±0.2, 13.4±0.2, 14.0±0.2, 15.0±0.2, and 17.2±0.2, wherein the PXRD pattern of crystalline Form G is measured at a temperature of about 25° C.

In one embodiment, crystalline Form G of Compound (I), mono benzenesulfonate is characterized by a powder x-ray diffraction pattern comprising five or more 2θ values (CuKα λ=1.5418 Å) selected from: 3.3±0.2, 6.2±0.2, 6.6±0.2, 7.9±0.2, 9.3±0.2, 9.9±0.2, 12.0±0.2, 12.5±0.2, 12.8±0.2, 13.4±0.2, 14.0±0.2, 15.0±0.2, and 17.2±0.2, wherein the PXRD pattern of crystalline Form G is measured at a temperature of about 25° C.

In one embodiment, crystalline Form G of Compound (I), mono benzenesulfonate is characterized by a powder x-ray diffraction pattern comprising six or more 2θ values (CuKα λ=1.5418 Å) selected from: 3.3±0.2, 6.2±0.2, 6.6±0.2, 7.9±0.2, 9.3±0.2, 9.9±0.2, 12.0±0.2, 12.5±0.2, 12.8±0.2, 13.4±0.2, 14.0±0.2, 15.0±0.2, and 17.2±0.2, wherein the PXRD pattern of crystalline Form G is measured at a temperature of about 25° C.

Figure 10:
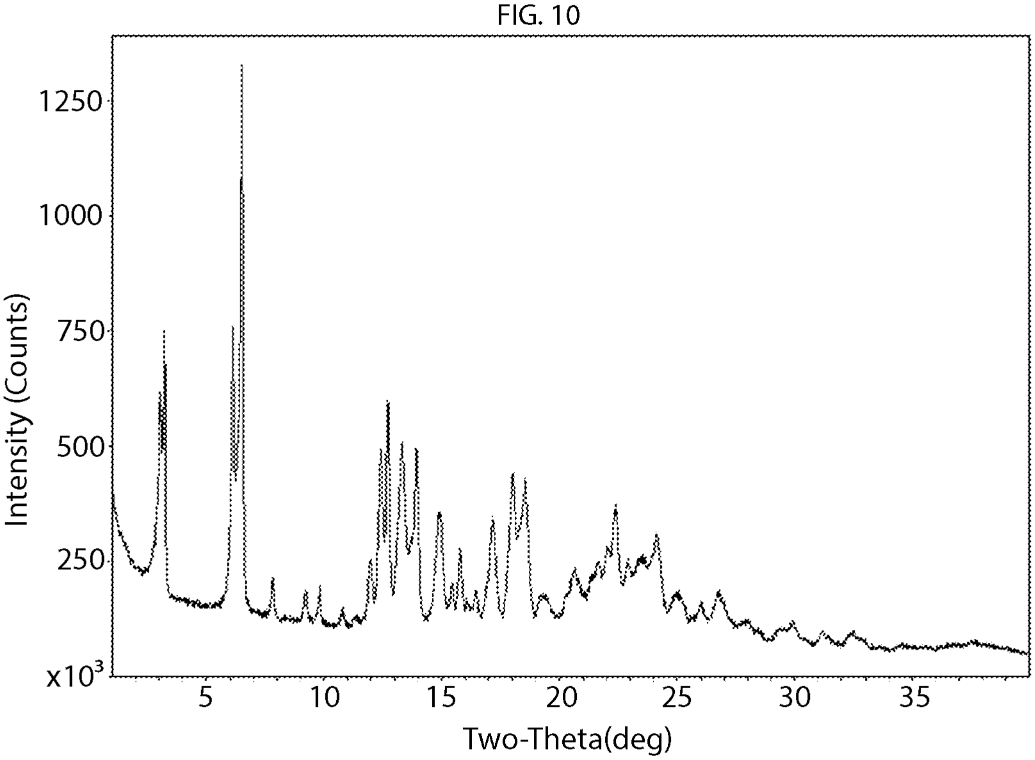
FIG. 10 shows the observed powder x-ray diffraction pattern (CuKα, λ=1.54178 Å at T=25° C.) of crystalline Form G of Compound (I), mono benzenesulfonic acid salt.

In one embodiment, crystalline Form G of Compound (I), mono benzenesulfonate is characterized by an observed powder x-ray diffraction pattern substantially as shown in FIG. 10.

In still yet an even further embodiment, crystalline Form G of Compound (I), mono benzenesulfonate is substantially pure.

In another embodiment, the crystalline form of Compound (I), mono benzenesulfonate consists essentially of crystalline Form G. The crystalline form of this embodiment may comprise at least about 90 wt. %, preferably at least about 95 wt. %, and more preferably at least about 99 wt. %, based on the weight of the crystalline form, crystalline Form G of Compound (I), mono benzenesulfonate salt.

One embodiment provides a composition comprising 2-(4-(2-(7,8-dimethyl-[1,2,4]triazolo[1,5-a]pyridin-6-yl)-3-isopropyl-1H-indol-5-yl) piperidin-1-yl)acetamide, mono benzenesulfonate salt, wherein at least 95 wt. %, preferably at least 97 wt. %, and more preferably at least 99 wt. % of said 2-(4-(2-(7,8-dimethyl-[1,2,4]triazolo[1,5-a]pyridin-6-yl)-3-isopropyl-1H-indol-5-yl) piperidin-1-yl)acetamide, mono benzenesulfonate is in crystalline Form G.

Form H of Compound (I), Mono Benzenesulfonate Anhydrate

In one embodiment, the mono benzenesulfonic acid salt of Compound (I) is provided as a crystalline material comprising crystalline Form H. The crystalline Form H of Compound (I), benzenesulfonic acid salt has a stoichiometry of 1:1 Compound (I) to benzenesulfonic acid. Crystalline Form H is an anhydrate. Crystalline Form H is also referred to herein as "Form H".

TABLE 8

Form H of Compound (I), Mono Benzenesulfonate Anhydrate Selected PXRD 2θ values (CuKα λ = 1.5418 Å) measured at room temperature

| | | | | | |
|---|---|---|---|---|---|
| 3.0 ± 0.2 | 3.3 ± 0.2 | 6.0 ± 0.2 | 6.7 ± 0.2 | 7.1 ± 0.2 | 10.6 ± 0.2 |
| 10.9 ± 0.2 | 11.4 ± 0.2 | 12.0 ± 0.2 | 12.4 ± 0.2 | 12.8 ± 0.2 | 13.3 ± 0.2 |
| 13.7 ± 0.2 | 14.1 ± 0.2 | 14.4 ± 0.2 | 14.8 ± 0.2 | 15.1 ± 0.2 | 15.6 ± 0.2 |
| 15.9 ± 0.2 | 16.2 ± 0.2 | 16.8 ± 0.2 | 17.2 ± 0.2 | 17.4 ± 0.2 | 17.9 ± 0.2 |
| 18.5 ± 0.2 | 18.9 ± 0.2 | 19.7 ± 0.2 | 20.1 ± 0.2 | 20.7 ± 0.2 | 21.3 ± 0.2 |
| 21.8 ± 0.2 | 22.2 ± 0.2 | 22.7 ± 0.2 | 23.0 ± 0.2 | 23.4 ± 0.2 | 23.7 ± 0.2 |
| 24.1 ± 0.2 | 24.7 ± 0.2 | 25.1 ± 0.2 | 25.7 ± 0.2 | 26.0 ± 0.2 | 26.4 ± 0.2 |
| 26.8 ± 0.2 | 27.3 ± 0.2 | 27.9 ± 0.2 | 28.6 ± 0.2 | 28.9 ± 0.2 | 29.8 ± 0.2 |

In one embodiment, crystalline Form H of Compound (I), mono benzenesulfonate is characterized by a powder x-ray diffraction pattern comprising four or more 2θ values (CuKα λ=1.5418 Å) selected from: 3.0±0.2, 3.3±0.2, 6.0±0.2, 6.7±0.2, 10.6±0.2, 11.4±0.2, 12.4±0.2, 15.6±0.2, 18.5±0.2, 21.3±0.2, and 22.7±0.2, wherein the PXRD pattern of crystalline Form H is measured at a temperature of about 25° C.

In one embodiment, crystalline Form H of Compound (I), mono benzenesulfonate is characterized by a powder x-ray diffraction pattern comprising five or more 2θ values (CuKα λ=1.5418 Å) selected from: 3.0±0.2, 3.3±0.2, 6.0±0.2, 6.7±0.2, 10.6±0.2, 11.4±0.2, 12.4±0.2, 15.6±0.2, 18.5±0.2, 21.3±0.2, and 22.7±0.2, wherein the PXRD pattern of crystalline Form H is measured at a temperature of about 25° C.

In one embodiment, crystalline Form H of Compound (I), mono benzenesulfonate is characterized by a powder x-ray diffraction pattern comprising six or more 2θ values (CuKα λ=1.5418 Å) selected from: 3.0±0.2, 3.3±0.2, 6.0±0.2, 6.7±0.2, 10.6±0.2, 11.4±0.2, 12.4±0.2, 15.6±0.2, 18.5±0.2, 21.3±0.2, and 22.7±0.2, wherein the PXRD pattern of crystalline Form H is measured at a temperature of about 25° C.

Figure 11:
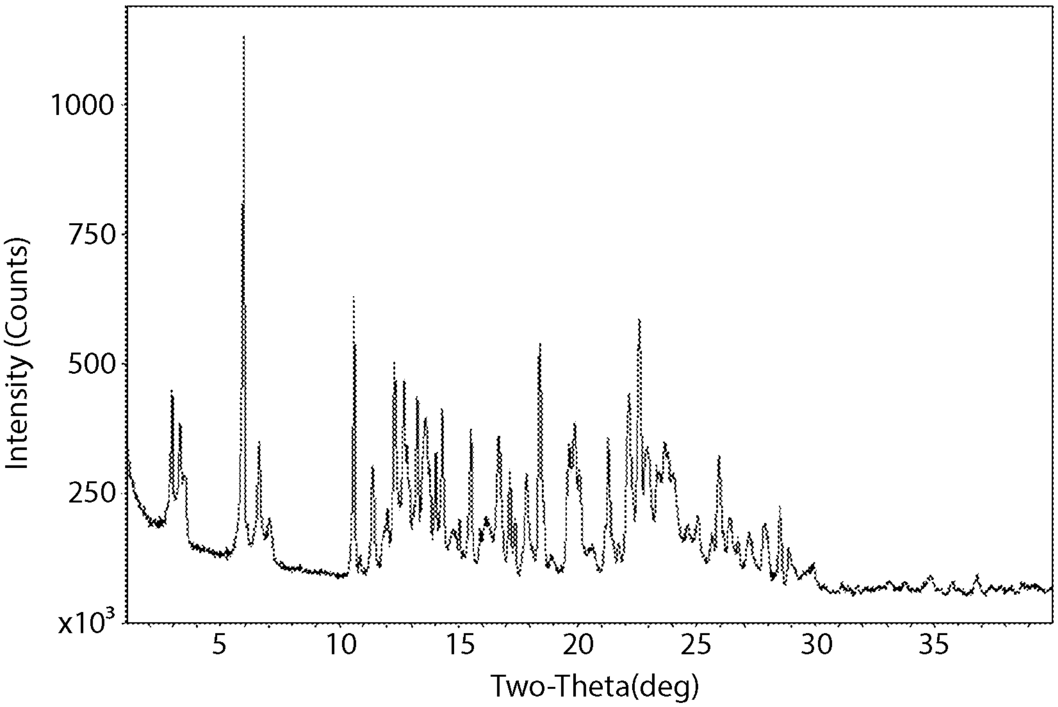
FIG. 11 shows the observed powder x-ray diffraction pattern (CuKα, λ=1.54178 Å at T=25° C.) of crystalline Form H of Compound (I), mono benzenesulfonic acid salt.

In one embodiment, crystalline Form H of Compound (I), mono benzenesulfonate is characterized by an observed powder x-ray diffraction pattern substantially as shown in FIG. 11.

In still yet an even further embodiment, crystalline Form H of Compound (I), mono benzenesulfonate is substantially pure.

In another embodiment, the crystalline form of Compound (I), mono benzenesulfonate consists essentially of crystalline Form H. The crystalline form of this embodiment may comprise at least about 90 wt. %, preferably at least about 95 wt. %, and more preferably at least about 99 wt. %, based on the weight of the crystalline form, crystalline Form H of Compound (I), mono benzenesulfonate salt.

One embodiment provides a composition comprising 2-(4-(2-(7,8-dimethyl-[1,2,4]triazolo[1,5-a]pyridin-6-yl)-3-isopropyl-1H-indol-5-yl) piperidin-1-yl)acetamide, mono benzenesulfonate salt, wherein at least 95 wt. 00 preferably at least 97 wt. %, and more preferably at least 99 wt. % of said 2-(4-(2-(7,8-dimethyl-[1,2,4]triazolo[1,5-a]pyridin-6-yl)-3-isopropyl-1H-indol-5-yl) piperidin-1-yl)acetamide, mono benzenesulfonate is in crystalline Form H.

Form I of Compound (I), Mono Hydrobromic Acid Salt Monohydrate

In one embodiment, the mono hydrobromic acid salt of Compound (I) is provided as a crystalline material comprising crystalline Form I. The crystalline Form I of Compound (I), mono hydrobromic acid salt has a stoichiometry of 1:1 Compound (I) to hydrobromic acid. Crystalline Form I is a monohydrate. Crystalline Form I is also referred to herein as "Form I".

TABLE 9

Form I of Compound (I), Mono Hydrobromic Acid Monohydrate Selected PXRD 2θ values (CuKα λ = 1.5418 Å) measured at room temperature

| | | | | | |
|---|---|---|---|---|---|
| 7.1 ± 0.2 | 8.7 ± 0.2 | 10.3 ± 0.2 | 11.8 ± 0.2 | 14.0 ± 0.2 | 15.1 ± 0.2 |
| 15.7 ± 0.2 | 16.3 ± 0.2 | 17.4 ± 0.2 | 17.9 ± 0.2 | 18.9 ± 0.2 | 20.6 ± 0.2 |
| 21.3 ± 0.2 | 21.9 ± 0.2 | 22.5 ± 0.2 | 22.9 ± 0.2 | 23.5 ± 0.2 | 24.4 ± 0.2 |
| 24.4 ± 0.2 | 25.1 ± 0.2 | 25.4 ± 0.2 | 26.0 ± 0.2 | 26.7 ± 0.2 | 28.1 ± 0.2 |
| 29.0 ± 0.2 | 29.5 ± 0.2 | 30.6 ± 0.2 | 31.5 ± 0.2 | 32.8 ± 0.2 | 34.2 ± 0.2 |
| 35.1 ± 0.2 | 36.5 ± 0.2 | 36.8 ± 0.2 | 38.2 ± 0.2 | — | — |

In one embodiment, crystalline Form I of Compound (I), mono hydrobromic acid is characterized by a powder x-ray diffraction pattern comprising four or more 2θ values (CuKα λ=1.5418 Å) selected from: 7.1±0.2, 8.7±0.2, 10.3±0.2, 11.8±0.2, 14.0±0.2, 16.3±0.2, 17.4±0.2, 17.9±0.2, 18.9±0.2, 21.3±0.2, and 22.5±0.2, wherein the PXRD pattern of crystalline Form I is measured at a temperature of about 25° C.

In one embodiment, crystalline Form I of Compound (I), mono hydrobromic acid is characterized by a powder x-ray diffraction pattern comprising five or more 2θ values (CuKα λ=1.5418 Å) selected from: 7.1±0.2, 8.7±0.2, 10.3±0.2, 11.8±0.2, 14.0±0.2, 16.3±0.2, 17.4±0.2, 17.9±0.2, 18.9±0.2, 21.3±0.2, and 22.5±0.2, wherein the PXRD pattern of crystalline Form I is measured at a temperature of about 25° C.

In one embodiment, crystalline Form I of Compound (I), mono hydrobromic acid is characterized by a powder x-ray diffraction pattern comprising six or more 2θ values (CuKα λ=1.5418 Å) selected from: 7.1±0.2, 8.7±0.2, 10.3±0.2, 11.8±0.2, 14.0±0.2, 16.3±0.2, 17.4±0.2, 17.9±0.2, 18.9±0.2, 21.3±0.2, and 22.5±0.2, wherein the PXRD pattern of crystalline Form I is measured at a temperature of about 25° C.

Figure 12:
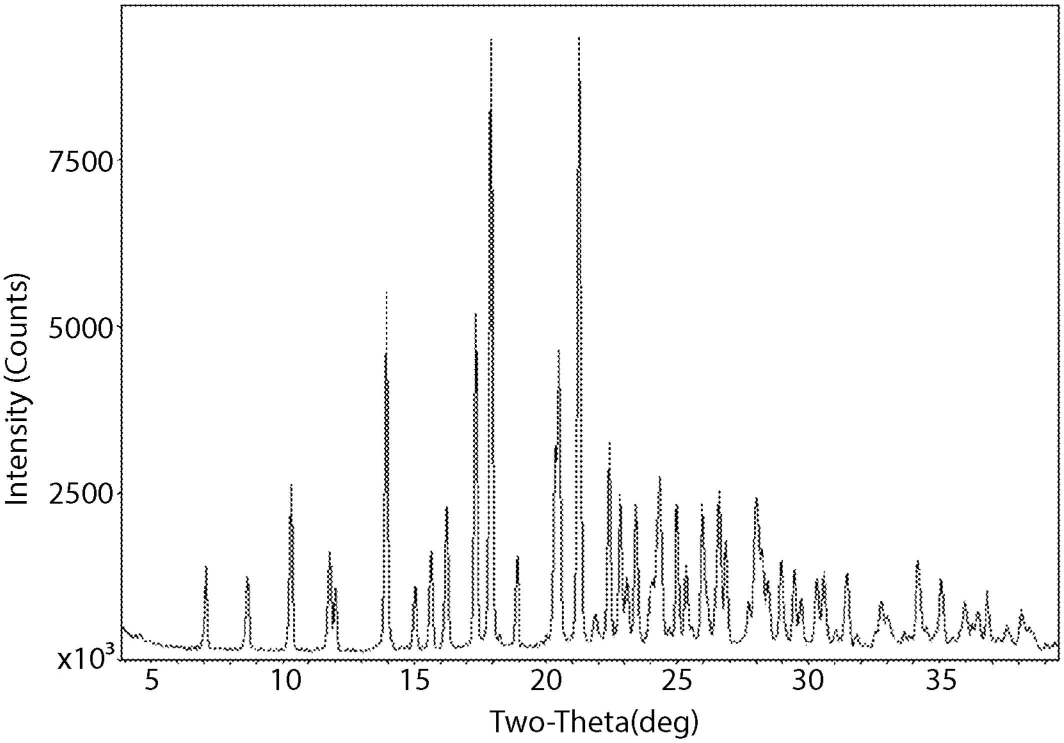
FIG. 12 shows the observed powder x-ray diffraction pattern (CuKα, λ=1.54178 Å at T=25° C.) of crystalline Form I of Compound (I), mono hydrobromic acid salt.

In one embodiment, crystalline Form I of Compound (I), mono hydrobromic acid is characterized by an observed powder x-ray diffraction pattern substantially as shown in FIG. 12.

In still yet an even further embodiment, crystalline Form I of Compound (I), mono hydrobromic acid is substantially pure.

In another embodiment, the crystalline form of Compound (I), mono hydrobromic acid consists essentially of crystalline Form I. The crystalline form of this embodiment may comprise at least about 90 wt. %, preferably at least about 95 wt. %, and more preferably at least about 99 wt. %, based on the weight of the crystalline form, crystalline Form I of Compound (I), mono hydrobromic acid salt.

One embodiment provides a composition comprising 2-(4-(2-(7,8-dimethyl-[1,2,4]triazolo[1,5-a]pyridin-6-yl)-3-isopropyl-1H-indol-5-yl) piperidin-1-yl)acetamide, mono hydrobromic acid salt, wherein at least 95 wt. 00 preferably at least 97 wt. %, and more preferably at least 99 wt. % of said 2-(4-(2-(7,8-dimethyl-[1,2,4]triazolo[1,5-a]pyridin-6-yl)-3-isopropyl-1H-indol-5-yl) piperidin-1-yl)acetamide, mono hydrobromic acid is in crystalline Form I.

Form J of Compound (I), Mono Citrate Anhydrate

In one embodiment, the citrate salt of Compound (I) is provided as a crystalline material comprising crystalline Form J. The crystalline Form J of Compound (I), citrate acid salt has a stoichiometry of 1:1 Compound (I) to citric acid. Crystalline Form J is an anhydrate. Crystalline Form J is also referred to herein as "Form J".

TABLE 10

Form J of Compound (I), Mono Citrate Anhydrate Selected PXRD 2θ values (CuKα λ = 1.5418 Å) measured at room temperature

| | | | | | |
|---|---|---|---|---|---|
| 3.6 ± 0.2 | 7.2 ± 0.2 | 9.4 ± 0.2 | 10.8 ± 0.2 | 12.3 ± 0.2 | 12.7 ± 0.2 |
| 13.4 ± 0.2 | 14.5 ± 0.2 | 15.4 ± 0.2 | 16.2 ± 0.2 | 18.5 ± 0.2 | 21.1 ± 0.2 |
| 22.9 ± 0.2 | 23.9 ± 0.2 | 28.3 ± 0.2 | — | — | — |

In one embodiment, crystalline Form J of Compound (I), mono citrate is characterized by a powder x-ray diffraction pattern comprising four or more 2θ values (CuKα λ=1.5418 Å) selected from: 3.6±0.2, 7.2±0.2, 10.8±0.2, 12.7±0.2, 13.4±0.2, 15.4±0.2, and 16.2±0.2, wherein the PXRD pattern of crystalline Form J is measured at a temperature of about 25° C.

In one embodiment, crystalline Form J of Compound (I), mono citrate is characterized by a powder x-ray diffraction pattern comprising five or more 2θ values (CuKα λ=1.5418 Å) selected from: 3.6±0.2, 7.2±0.2, 10.8±0.2, 12.7±0.2, 13.4±0.2, 15.4±0.2, and 16.2±0.2, wherein the PXRD pattern of crystalline Form J is measured at a temperature of about 25° C.

In one embodiment, crystalline Form J of Compound (I), mono citrate is characterized by a powder x-ray diffraction pattern comprising six or more 2θ values (CuKα λ=1.5418 Å) selected from: 3.6±0.2, 7.2±0.2, 10.8±0.2, 12.7±0.2, 13.4±0.2, 15.4±0.2, and 16.2±0.2, wherein the PXRD pattern of crystalline Form J is measured at a temperature of about 25° C.

Figure 13:
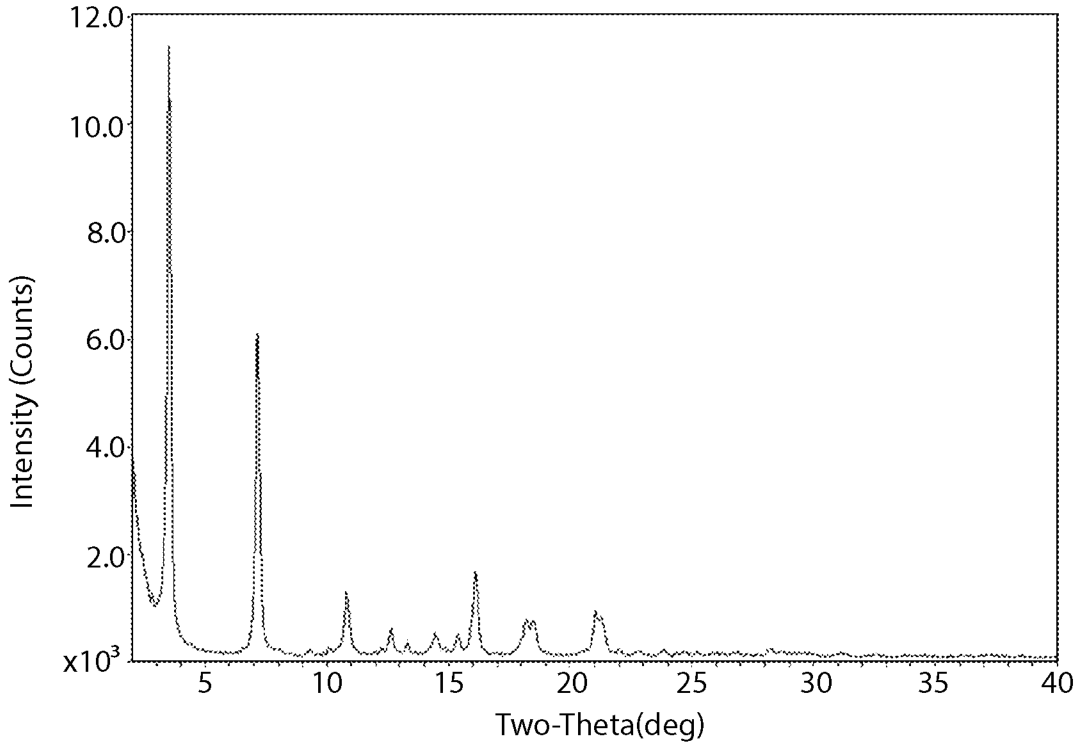
FIG. 13 shows the observed powder x-ray diffraction pattern (CuKα, λ=1.54178 Å at T=25° C.) of crystalline Form J of Compound (I), mono citric acid salt.

In one embodiment, crystalline Form J of Compound (I), mono citrate is characterized by an observed powder x-ray diffraction pattern substantially as shown in FIG. 13.

In still yet an even further embodiment, crystalline Form J of Compound (I), mono citrate is substantially pure.

In another embodiment, the crystalline form of Compound (I), mono citrate consists essentially of crystalline Form J. The crystalline form of this embodiment may comprise at least about 90 wt. %, preferably at least about 95 wt. %, and more preferably at least about 99 wt. %, based on the weight of the crystalline form, crystalline Form J of Compound (I), mono citrate salt.

One embodiment provides a composition comprising 2-(4-(2-(7,8-dimethyl-[1,2,4]triazolo[1,5-a]pyridin-6-yl)-3-isopropyl-1H-indol-5-yl) piperidin-1-yl)acetamide, mono citrate salt, wherein at least 95 wt. %, preferably at least 97 wt. %, and more preferably at least 99 wt. % of said 2-(4-(2-(7,8-dimethyl-[1,2,4]triazolo[1,5-a]pyridin-6-yl)-3-isopropyl-1H-indol-5-yl) piperidin-1-yl)acetamide, mono citrate is in crystalline Form J.

Form K of Compound (I), Mono Hydrochloric Acid Anhydrate

In one embodiment, the hydrochloric acid salt of Compound (I) is provided as a crystalline material comprising crystalline Form K. The crystalline Form K of Compound (I), hydrochloric acid salt has a stoichiometry of 1:1 Compound (I) to hydrochloric acid. Crystalline Form is an anhydrate. Crystalline Form K is also referred to herein as "Form K".

TABLE 11

Form K of Compound (I), Mono Hydrochloric Acid Selected PXRD 2θ values (CuKα λ = 1.5418 Å) measured at room temperature

| | | | | | |
|---|---|---|---|---|---|
| 5.8 ± 0.2 | 8.7 ± 0.2 | 11.4 ± 0.2 | 13.1 ± 0.2 | 13.9 ± 0.2 | 14.3 ± 0.2 |
| 14.6 ± 0.2 | 15.2 ± 0.2 | 17.5 ± 0.2 | 18.0 ± 0.2 | 19.2 ± 0.2 | 19.7 ± 0.2 |
| 20.6 ± 0.2 | 21.7 ± 0.2 | 22.0 ± 0.2 | 23.2 ± 0.2 | 23.9 ± 0.2 | 24.6 ± 0.2 |
| 25.0 ± 0.2 | 26.0 ± 0.2 | 26.4 ± 0.2 | 27.0 ± 0.2 | 28.0 ± 0.2 | 29.2 ± 0.2 |
| 30.7 ± 0.2 | 32.0 ± 0.2 | — | — | — | — |

In one embodiment, crystalline Form K of Compound (I), mono hydrochloric acid is characterized by a powder x-ray diffraction pattern comprising four or more 2θ values (CuKα λ=1.5418 Å) selected from: 5.8±0.2, 8.7±0.2, 11.4±0.2, 13.1±0.2, 13.9±0.2, 17.5±0.2, 19.2±0.2, 19.7±0.2, 20.6±0.2, and 22.0±0.2, wherein the PXRD pattern of crystalline Form K is measured at a temperature of about 25° C.

In one embodiment, crystalline Form K of Compound (I), mono hydrochloric acid is characterized by a powder x-ray diffraction pattern comprising five or more 2θ values (CuKα λ=1.5418 Å) selected from: 5.8±0.2, 8.7±0.2, 11.4±0.2, 13.1±0.2, 13.9±0.2, 17.5±0.2, 19.2±0.2, 19.7±0.2, 20.6±0.2, and 22.0±0.2, wherein the PXRD pattern of crystalline Form K is measured at a temperature of about 25° C.

In one embodiment, crystalline Form K of Compound (I), mono hydrochloric acid is characterized by a powder x-ray diffraction pattern comprising six or more 2θ values (CuKα λ=1.5418 Å) selected from: 5.8±0.2, 8.7±0.2, 11.4±0.2, 13.1±0.2, 13.9±0.2, 17.5±0.2, 19.2±0.2, 19.7±0.2, 20.6±0.2, and 22.0±0.2, wherein the PXRD pattern of crystalline Form K is measured at a temperature of about 25° C.

Figure 14:
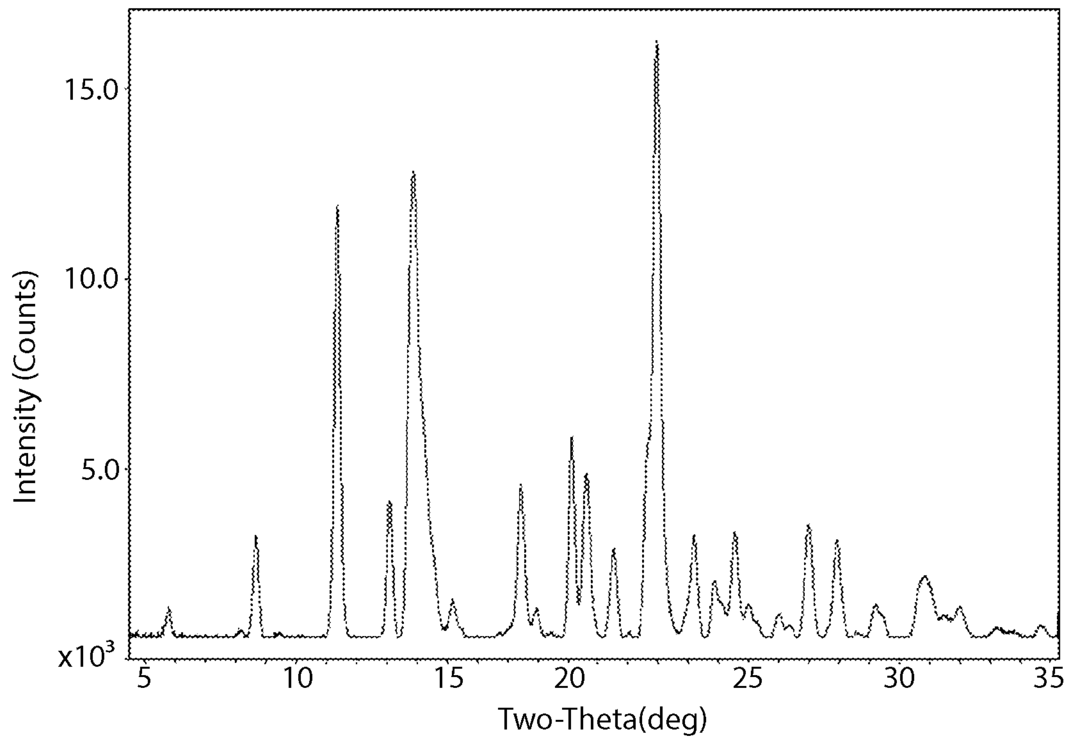
FIG. 14 shows the observed powder x-ray diffraction pattern (CuKα, λ=1.54178 Å at T=25° C.) of crystalline Form K of Compound (I), mono hydrochloric acid salt.

In one embodiment, crystalline Form K of Compound (I), mono hydrochloric acid is characterized by an observed powder x-ray diffraction pattern substantially as shown in FIG. 14.

In still yet an even further embodiment, crystalline Form K of Compound (I), mono hydrochloric acid is substantially pure.

In another embodiment, the crystalline form of Compound (I), mono hydrochloric acid consists essentially of crystalline Form K. The crystalline form of this embodiment may comprise at least about 90 wt. %, preferably at least about 95 wt. %, and more preferably at least about 99 wt. %, based on the weight of the crystalline form, crystalline Form K of Compound (I), mono hydrochloric acid salt.

One embodiment provides a composition comprising 2-(4-(2-(7,8-dimethyl-[1,2,4]triazolo[1,5-a]pyridin-6-yl)-3-isopropyl-1H-indol-5-yl) piperidin-1-yl)acetamide, mono hydrochloric acid salt, wherein at least 95 wt. %, preferably at least 97 wt. %, and more preferably at least 99 wt. % of said 2-(4-(2-(7,8-dimethyl-[1,2,4]triazolo[1,5-a]pyridin-6-yl)-3-isopropyl-1H-indol-5-yl) piperidin-1-yl)acetamide, mono hydrochloric acid is in crystalline Form K.

Form L of Compound (I), Mono Hydrochloric Acid Monohydrate

In one embodiment, the hydrochloric acid salt of Compound (I) is provided as a crystalline material comprising crystalline Form L. The crystalline Form L of Compound (I), hydrochloric acid bromide salt has a stoichiometry of 1:1 Compound (I) to hydrochloric acid. Crystalline Form is a monohydrate. Crystalline Form L is also referred to herein as "Form L".

TABLE 12

Form L of Compound (I), Mono Hydrochloric Acid Monohydrate Selected PXRD 2θ values (CuKα λ = 1.5418 Å) measured at room temperature

| | | | | | |
|---|---|---|---|---|---|
| 3.8 ± 0.2 | 7.8 ± 0.2 | 12.9 ± 0.2 | 14.0 ± 0.2 | 14.4 ± 0.2 | 15.3 ± 0.2 |
| 16.3 ± 0.2 | 19.4 ± 0.2 | 21.6 ± 0.2 | 23.2 ± 0.2 | 27.8 ± 0.2 | 31.9 ± 0.2 |

In one embodiment, crystalline Form L of Compound (I), mono hydrochloric acid is characterized by a powder x-ray diffraction pattern comprising four or more 2θ values (CuKα λ=1.5418 Å) selected from: 3.8±0.2, 7.8±0.2, 12.9±0.2, 14.4±0.2, 15.3±0.2, 16.3±0.2, 21.6±0.2, 23.2±0.2, 27.8±0.2, and 31.9±0.2, wherein the PXRD pattern of crystalline Form L is measured at a temperature of about 25° C.

In one embodiment, crystalline Form L of Compound (I), mono hydrochloric acid is characterized by a powder x-ray diffraction pattern comprising five or more 2θ values (CuKα λ=1.5418 Å) selected from: 3.8±0.2, 7.8±0.2, 12.9±0.2, 14.4±0.2, 15.3±0.2, 16.3±0.2, 21.6±0.2, 23.2±0.2, 27.8±0.2, and 31.9±0.2, wherein the PXRD pattern of crystalline Form L is measured at a temperature of about 25° C.

In one embodiment, crystalline Form L of Compound (I), mono hydrochloric acid is characterized by a powder x-ray diffraction pattern comprising six or more 2θ values (CuKα λ=1.5418 Å) selected from: 3.8±0.2, 7.8±0.2, 12.9±0.2, 14.4±0.2, 15.3±0.2, 16.3±0.2, 21.6±0.2, 23.2±0.2, 27.8±0.2, and 31.9±0.2, wherein the PXRD pattern of crystalline Form L is measured at a temperature of about 25° C.

Figure 15:
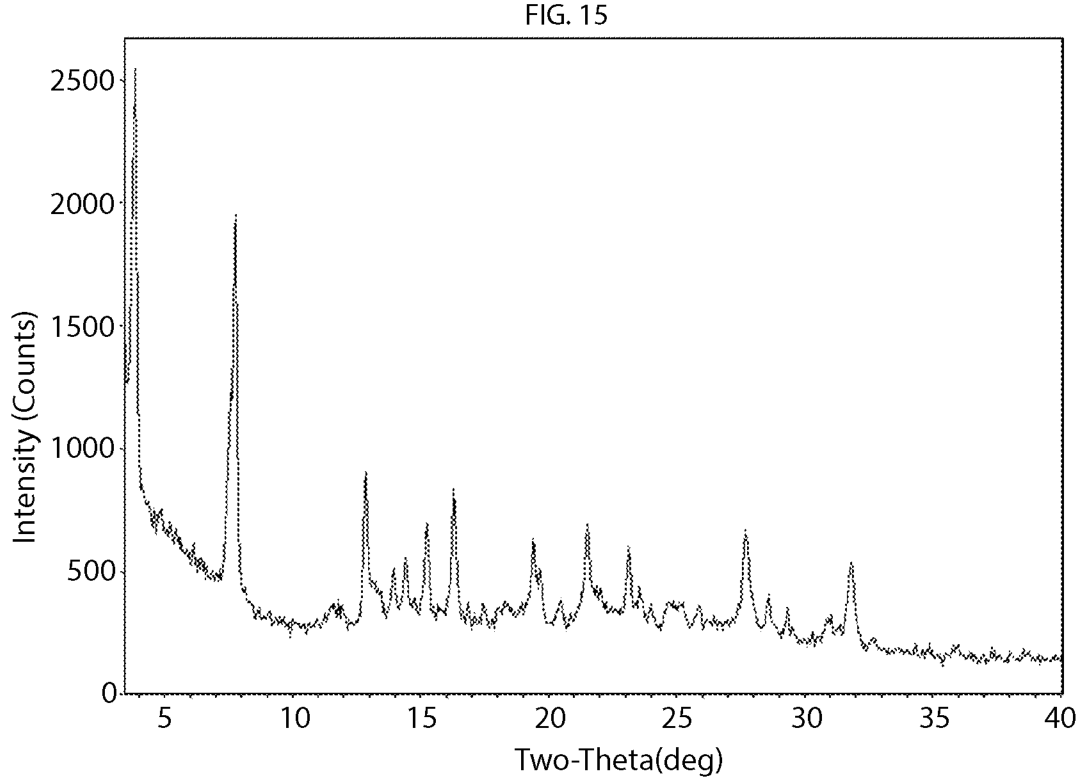
FIG. 15 shows the observed powder x-ray diffraction pattern (CuKα, λ=1.54178 Å at T=25° C.) of crystalline Form L of Compound (I), mono hydrochloric acid salt.

In one embodiment, crystalline Form L of Compound (I), mono hydrochloric acid is characterized by an observed powder x-ray diffraction pattern substantially as shown in FIG. 15.

In still yet an even further embodiment, crystalline Form L of Compound (I), mono hydrochloric acid is substantially pure.

In another embodiment, the crystalline form of Compound (I), mono hydrochloric acid consists essentially of crystalline Form L. The crystalline form of this embodiment may comprise at least about 90 wt. %, preferably at least about 95 wt. %, and more preferably at least about 99 wt. %, based on the weight of the crystalline form, crystalline Form L of Compound (I), mono hydrochloric acid salt.

One embodiment provides a composition comprising 2-(4-(2-(7,8-dimethyl-[1,2,4]triazolo[1,5-a]pyridin-6-yl)-3-isopropyl-1H-indol-5-yl) piperidin-1-yl)acetamide, mono hydrochloric acid salt, wherein at least 95 wt. %, preferably at least 97 wt. %, and more preferably at least 99 wt. % of said 2-(4-(2-(7,8-dimethyl-[1,2,4]triazolo[1,5-a]pyridin-6-yl)-3-isopropyl-1H-indol-5-yl) piperidin-1-yl)acetamide, mono hydrochloric acid is in crystalline Form L.

Form M of Compound (I), Mono Methane Sulfonic Acid Salt Monohydrate

In one embodiment, the methane sulfonic acid salt of Compound (I) is provided as a crystalline material comprising crystalline Form M. The crystalline Form M of Compound (I), methane sulfonic acid bromide salt has a stoichiometry of 1:1 Compound (I) to methane sulfonic acid. Crystalline Form M is a monohydrate. Crystalline Form M is also referred to herein as "Form M".

TABLE 13

Form M of Compound (I), Mono Methane Sulfonic Acid Salt Monohydrate Selected PXRD 2θ values (CuKα λ = 1.5418 Å) measured at room temperature

| | | | | | |
|---|---|---|---|---|---|
| 13.5 ± 0.2 | 14.7 ± 0.2 | 15.3 ± 0.2 | 15.9 ± 0.2 | 17.6 ± 0.2 | 20.3 ± 0.2 |
| 21.1 ± 0.2 | 21.5 ± 0.2 | 22.7 ± 0.2 | 23.2 ± 0.2 | 23.9 ± 0.2 | 24.3 ± 0.2 |
| 25.0 ± 0.2 | 26.3 ± 0.2 | 27.1 ± 0.2 | 28.3 ± 0.2 | 28.8 ± 0.2 | 29.8 ± 0.2 |
| 30.7 ± 0.2 | 31.2 ± 0.2 | 31.7 ± 0.2 | 32.3 ± 0.2 | 33.2 ± 0.2 | 33.6 ± 0.2 |
| 34.6 ± 0.2 | 35.2 ± 0.2 | — | — | — | — |

In one embodiment, crystalline Form M of Compound (I), mono methane sulfonic acid salt is characterized by a powder x-ray diffraction pattern comprising four or more 2θ values (CuKα λ=1.5418 Å) selected from: 13.5±0.2, 14.7±0.2, 15.3±0.2, 15.9±0.2, 17.6±0.2, 20.3±0.2, 21.1±0.2, 22.7±0.2, 23.2±0.2, 23.9±0.2, and 24.3±0.2, wherein the PXRD pattern of crystalline Form M is measured at a temperature of about 25° C.

In one embodiment, crystalline Form M of Compound (I), mono methane sulfonic acid salt is characterized by a powder x-ray diffraction pattern comprising five or more 2θ values (CuKα λ=1.5418 Å) selected from: 13.5±0.2, 14.7±0.2, 15.3±0.2, 15.9±0.2, 17.6±0.2, 20.3±0.2, 21.1±0.2, 22.7±0.2, 23.2±0.2, 23.9±0.2, and 24.3±0.2, wherein the PXRD pattern of crystalline Form M is measured at a temperature of about 25° C.

In one embodiment, crystalline Form M of Compound (I), mono methane sulfonic acid salt is characterized by a powder x-ray diffraction pattern comprising six or more 2θ values (CuKα λ=1.5418 Å) selected from: 13.5±0.2, 14.7±0.2, 15.3±0.2, 15.9±0.2, 17.6±0.2, 20.3±0.2, 21.1±0.2, 22.7±0.2, 23.2±0.2, 23.9±0.2, and 24.3±0.2, wherein the PXRD pattern of crystalline Form M is measured at a temperature of about 25° C.

Figure 16:
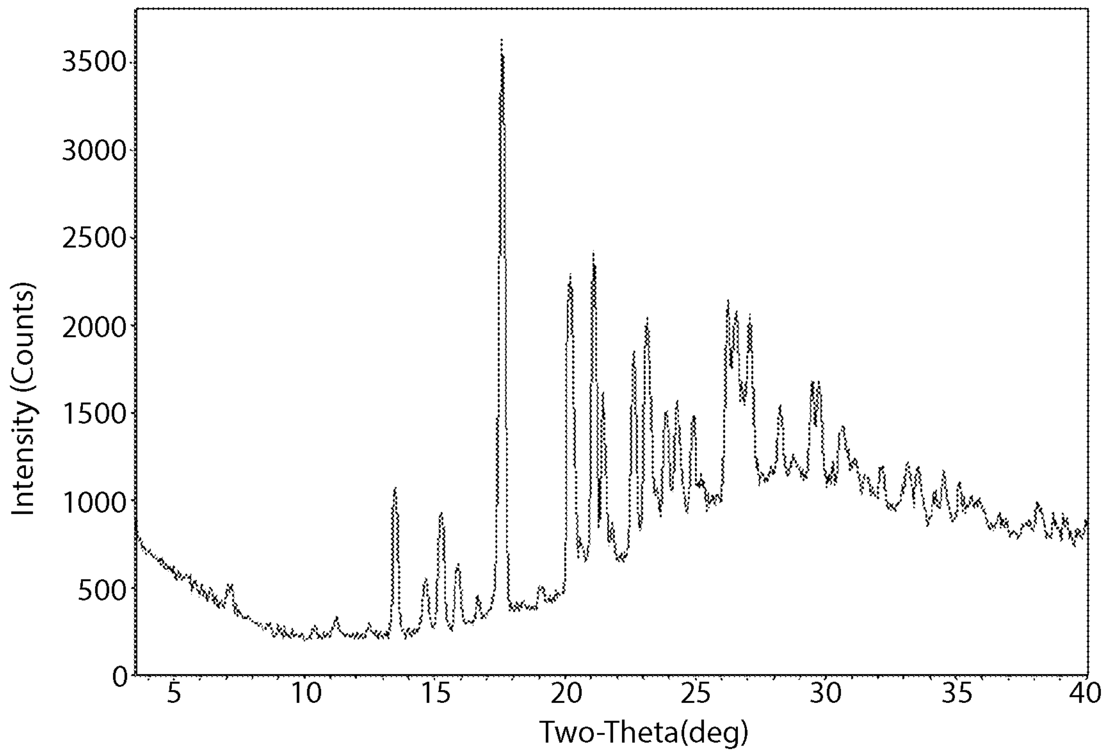
FIG. 16 shows the observed powder x-ray diffraction pattern (CuKα, λ=1.54178 Å at T=25° C.) of crystalline Form M of Compound (I), mono methane sulfonic acid salt.

In one embodiment, crystalline Form M of Compound (I), mono methane sulfonic acid salt is characterized by an observed powder x-ray diffraction pattern substantially as shown in FIG. 16.

In still yet an even further embodiment, crystalline Form M of Compound (I), mono methane sulfonic acid salt is substantially pure.

In another embodiment, the crystalline form of Compound (I), mono methane sulfonic acid salt consists essentially of crystalline Form M. The crystalline form of this embodiment may comprise at least about 90 wt. %, preferably at least about 95 wt. %, and more preferably at least about 99 wt. %, based on the weight of the crystalline form, crystalline Form M of Compound (I), mono methane sulfonic acid salt.

One embodiment provides a composition comprising 2-(4-(2-(7,8-dimethyl-[1,2,4]triazolo[1,5-a]pyridin-6-yl)-3-isopropyl-1H-indol-5-yl) piperidin-1-yl)acetamide, mono methane sulfonic acid salt, wherein at least 95 wt. %, preferably at least 97 wt. %, and more preferably at least 99 wt. % of said 2-(4-(2-(7,8-dimethyl-[1,2,4]triazolo[1,5-a]pyridin-6-yl)-3-isopropyl-1H-indol-5-yl) piperidin-1-yl)acetamide, mono methane sulfonic acid salt is in crystalline Form M.

Crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. High throughput crystallization techniques may be employed to prepare crystalline forms including polymorphs.

Crystals of drugs, including polymorphs, methods of preparation, and characterization of drug crystals are discussed in *Solid-State Chemistry of Drugs*, S. R. Byrn, R. R. Pfeiffer, and J. G. Stowell, $2^{nd}$ Edition, SSCI, West Lafayette, Indiana (1999).

For crystallization techniques that employ solvent, the choice of solvent or solvents is typically dependent upon one or more factors, such as solubility of the compound, crystallization technique, and vapor pressure of the solvent. Combinations of solvents may be employed, for example, the compound may be solubilized into a first solvent to afford a solution, followed by the addition of an antisolvent to decrease the solubility of the compound in the solution and to afford the formation of crystals. An antisolvent is a solvent in which the compound has low solubility.

In one method to prepare crystals, a compound is suspended and/or stirred in a suitable solvent to afford a slurry, which may be heated to promote dissolution. The term "slurry", as used herein, means a saturated solution of the compound, which may also contain an additional amount of the compound to afford a heterogeneous mixture of the compound and a solvent at a given temperature.

Seed crystals may be added to any crystallization mixture to promote crystallization. Seeding may be employed to control growth of a particular polymorph or to control the particle size distribution of the crystalline product. Accordingly, calculation of the amount of seeds needed depends on the size of the seed available and the desired size of an average product particle as described, for example, in "Programmed Cooling of Batch Crystallizers," J. W. Mullin and J. Nyvlt, *Chemical Engineering Science,* 1971, 26, 369-377. In general, seeds of small size are needed to control effectively the growth of crystals in the batch. Seed of small size may be generated by sieving, milling, or micronizing of large crystals, or by micro-crystallization of solutions. Care should be taken that milling or micronizing of crystals does not result in any change in crystallinity form the desired crystal form (i.e., change to amorphous or to another polymorph).

A cooled crystallization mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as solid-state nuclear magnetic resonance, differential scanning calorimetry, powder x-ray diffraction, or the like, to assure formation of the preferred crystalline form of the product. The resulting crystalline form is typically produced in an amount of greater than about 70 weight % isolated yield, preferably greater than 90 weight % isolated yield, based on the weight of the compound originally employed in the crystallization procedure. The product may be comilled or passed through a mesh screen to delump the product, if necessary.

Crystalline forms may be prepared directly from the reaction medium of the final process for preparing Compound (I). This may be achieved, for example, by employing in the final process step a solvent or a mixture of solvents from which Compound (I) may be crystallized. Alternatively, crystalline forms may be obtained by distillation or solvent addition techniques. Suitable solvents for this purpose include, for example, the aforementioned nonpolar solvents and polar solvents, including protic polar solvents such as alcohols, and aprotic polar solvents such as ketones.

The presence of more than one polymorph in a sample may be determined by techniques such as powder x-ray diffraction (PXRD) or solid-state nuclear magnetic resonance spectroscopy. For example, the presence of extra peaks in the comparison of an experimentally measured PXRD pattern with a simulated PXRD pattern may indicate more than one polymorph in the sample. The simulated PXRD may be calculated from single crystal x-ray data. see Smith, D. K., "*A FORTRAN Program for Calculating X-Ray Powder Diffraction Patterns*," Lawrence Radiation Laboratory, Livermore, California, UCRL-7196 (April 1963).

The forms of Compound (I) may be characterized using various techniques, the operation of which are well known to those of ordinary skill in the art. The forms may be characterized and distinguished using single crystal x-ray diffraction, which is based on unit cell measurements of a single crystal at a fixed analytical temperature. A detailed description of unit cells is provided in Stout & Jensen, X-Ray Structure Determination: A Practical Guide, Macmillan Co., New York (1968), Chapter 3, which is herein incorporated by reference. Alternatively, another means of characterizing the crystalline structure is by powder x-ray diffraction analysis in which the diffraction profile is compared to a simulated profile representing pure powder material, both run at the same analytical temperature, and measurements for the subject form characterized as a series of 2θ values (usually four or more).

Other means of characterizing the form may be used, such as solid-state nuclear magnetic resonance (ssNMR), differential scanning calorimetry, thermal analysis, and vibrational spectroscopy. These parameters may also be used in combination to characterize the subject form.

UTILITY

The mono benzenesulfonic acid salt of Compound (I) can be used to isolate Compound (I) from other components at the completion of the synthesis process; and/or to purify Compound (I) by one or a series of crystallization steps.

Crystalline Form A of the mono benzenesulfonic acid salt of Compound (I) can be used to isolate Compound (I) from other components at the completion of the synthesis process; and/or to purify Compound (I) by one or a series of crystallization steps. The isolation and the purification steps can be combined or practiced as separate process steps.

The mono benzenesulfonic acid salt of Compound (I) can be formulated into a pharmaceutical composition suitable for oral administration.

Crystalline Form A of the mono benzenesulfonic acid salt of Compound (I) can be formulated into a pharmaceutical composition suitable for oral administration.

In another aspect, the invention relates to a method of treating lupus (such as systemic lupus erythematosus (SLE) or cutaneous lupus erythematosus (CLE)) in a human patient in need thereof comprising orally administering to the patient an effective amount of any salt of Compound (I) as described herein.

EXAMPLES

The invention will now be further described by the following working example(s), which are preferred embodiments of the invention. All temperatures are in degrees Celsius (° C.) unless otherwise indicated. These examples are illustrative rather than limiting and it is to be understood that there may be other embodiments that fall within the spirit and scope of the invention as defined by the claims appended hereto.

The synthesis of Compound (I) is disclosed in WO 2018/005586 as Example 15.

Preparation 1: Free Base, Hemihydrate Crystalline Form

Compound (I) (100 mg) was dissolved in 1 mL DMF at 41° C. Sample was cooled to room temperature and 0.2 mL water was added to form a slurry. The slurry was stirred at room temperature for 2 days. The solids in the slurry were a free base, hemihydrate crystalline form.

Preparation 2: Free Base, Hemihydrate Crystalline Form

Compound (I) (1.15 g) was dissolved in 95:5 THF:water (vol:vol) at room temperature. Next, 1 mL of the solution was transferred to vials. The vials were placed in a vacuum concentrator to evaporate the solvent from each of the vials.

To one vial, 1 mL of 90:10 DCM:MeOH (vol:vol) was added and the slurry was stirred for 13 days. The solids in the slurry were a free base, hemihydrate crystalline form.

To another vial, 1 mL of 1 mL MIBK was added and the slurry was stirred for 13 days. The solids in the slurry were a free base, hemihydrate crystalline form.

Example 1: Preparation of Crystalline Form a of Compound (I), Mono Benzenesulfonate Compound (I) (1 g of free base, hemihydrate crystalline form) was slurried in 10 mL of THF:water (0.98:0.02) (vol:vol). Next, 1.360 mL of 2 M aqueous benzenesulfonic acid was added dropwise and the mixture was stirred at 700 rpm overnight at 20° C. The slurry was dried in a vacuum oven at 65° C. overnight. Next, 150 mg of the dried solids was slurried in water at 20° C. with stirring. The slurry was placed in a vacuum oven at 65° C. and dried overnight to afford Form A of Compound (I), mono benzenesulfonate, as determined by PXRD.

Example 2: Preparation of Crystalline Form A of Compound (I), Mono Benzenesulfonate Compound (I) (2 g of free base, hemihydrate crystalline form) was slurried in 10 mL of acetonitrile. The slurry was stirred for 5 minutes at 400 rpm speed at 20° C. Next, 2 M aqueous benzenesulfonic acid (0.6 eq. 1.35 mL) was added to the slurry. The slurry was stirred for 5 minutes. An additional 0.6 eq. (1.35 mL) of 2 M aqueous benzenesulfonic acid was added. The slurry was stirred for 5 mins, followed by addition of 0.5 eq. (1.125 mL) of 2 M aqueous benzenesulfonic acid. This slurry was stirred at 400 rpm for 3 hours at 20° C. The slurry solids were Form A of Compound (I), mono benzenesulfonate as determined by PXRD. The slurry solids were isolated by filtration, and washed twice with the mother liquor. The solids were dried at 65° C. in a vacuum oven with 180 mm Hg vacuum for 2 days to afford Form A of Compound (I), mono benzenesulfonate, as determined by PXRD. Form A was maintained during the drying of the slurry under the described drying conditions.

Example 3: General Preparation of Crystalline Form C of Compound (I), Mono Benzenesulfonate Solvate A slurry is prepared by adding sufficient solids of crystalline Form A of Compound (I), mono benzenesulfonate to a solvent (acetone, acetonitrile, dichloromethane, dimethyl formamide, dimethylsulfoxide, isopropanol, isopropyl acetate, methyl isobutyl ketone, and tetrahydrofuran) at a temperature in the range of room temperature to 60° C. such that undissolved solids are present. The slurry is stirred at room temperature to 60° C. for 5-13 days. The solids from the slurry are collected via vacuum filtration and analyzed by PXRD.

Crystalline Form C of Compound (I), Monobenzenesulfonate Acetonitrile Solvate

A slurry was prepared by adding sufficient solids of crystalline Form A of Compound (I), mono benzenesulfonate to acetonitrile at 60° C. such that undissolved solids were present. The slurry was stirred at room temperature for 13 days. The solids from the slurry were collected via vacuum filtration and analyzed by PXRD.

Example 4: Preparation of Crystalline Form D of Compound (I), Mono Benzenesulfonate Crystalline Form A of Compound (I), mono benzenesulfonate, was dried in a vacuum oven set at 70° C. for 3 days to afford crystalline Form D of Compound (I). The solids were analyzed via PXRD.

Example 5: Preparation of Crystalline Form E of Compound (I), Mono Benzenesulfonate Crystalline Form C of Compound (I), mono benzenesulfonate, was dried in a vacuum oven set at 55° C. for 1 day to afford crystalline Form E of Compound (I). The solids were analyzed via PXRD.

Example 6: Preparation of Crystalline Form F of Compound (I), Mono Benzenesulfonate A slurry was prepared by adding sufficient solids of crystalline Form A of Compound (I), mono benzenesulfonate, to ethyl acetate at 60° C. such that undissolved solids were present. The slurry was stirred at 60° C. for 5 days. The solids from the slurry were collected via vacuum filtration and dried in a vacuum oven set at 55° C. for 1 day. The solids were analyzed via PXRD.

Example 7: Preparation of Crystalline Form G of Compound (I), Mono Benzenesulfonate A slurry was prepared by adding sufficient solids of crystalline Form A of Compound (I), mono benzenesulfonate, to methanol at room temperature such that undissolved solids were present. The slurry was stirred at room temperature for 13 days. The solids from the slurry were collected via vacuum filtration and dried in a vacuum oven set at 55° C. for 1 day. The solids were analyzed via PXRD.

Example 8: Preparation of Crystalline Form H of Compound (I), Mono Benzenesulfonate A slurry was prepared by adding sufficient solids of crystalline Form A of Compound (I), mono benzenesulfonate, to ethanol at 60° C. such that undissolved solids were present. The slurry was stirred at 60° C. for 6 days. In another vial, a slurry of Form A was prepared by adding sufficient solids to ethanol at room temperature such that undissolved solids were present. The slurry was stirred at room temperature for 13 days. The solids in the two vials were combined in ethanol. The slurry was stirred at 60° C. for 8 days and at room temperature for 2 days. The solids from the slurry were collected via vacuum filtration and dried in a vacuum oven set at 55° C. for 1 day. The solids were analyzed via PXRD.

Example 9: Preparation of Crystalline Form I of Compound (I), Mono Hydrobromic acid Salt Compound (I), free base, hemihydrate crystalline form (1 g) was slurried in 10 mL of THF:water (0.98:0.02) v/v and kept stirring at 20° C. at 700 rpm. Next, 1360 μL of 2 M aqueous hydrobromic acid was added dropwise and the slurry was stirred overnight at 20° C. for 12 hours at 700 rpm. The sample was dried in a vacuum oven without filtration at 65° C. for 12 hours. The solids were characterized by PXRD.

Example 10: Preparation of Crystalline Form J of Compound (I), Mono Citrate

Compound (I), free base, hemihydrate crystalline form (800 mg) was slurried in 6 mL of THF at 20° C. stirring at 700 rpm. Next, 214 μL of 1 M citric acid monohydrate (ethanolic) was added dropwise and stirred 12 hours at 700 rpm at 20° C. The slurry was dried in a vacuum oven without filtration at 65° C. for 12 hours. A sample of the solids (50 mg) was slurried in 0.5 mL of acetonitrile at 20° C. while stirring at 700 rpm for 5 days. The sample was dried in a vacuum oven without filtration at 65° C. for 12 hours. Solids were then analyzed by PXRD.

Example 11: Preparation of Crystalline Form K of Compound (I), Hydrochloric Acid Salt Compound (I), free base, hemihydrate crystalline form (8 mg) and 1 equivalent of HCl were added to 0.3 mL of THF in a small vial at room temperature. The solids were analyzed by PXRD.

Example 12: Preparation of Crystalline Form K of Compound (I), Hydrochloric Acid Salt Compound (I), free base, hemihydrate crystalline form (8 mg) and 1 equivalent of HCl were added to 0.3 mL of acetonitrile in a small vial at room temperature. The solids were analyzed by PXRD.

Example 13: Preparation of Crystalline Form K of Compound (I), Hydrochloric Acid Salt Compound (I), free base, hemihydrate crystalline form (8 mg) and 1 equivalent of HCl were added to 0.3 mL of methanol in a small vial at room temperature. The solids were analyzed by PXRD.

Example 14: Preparation of Crystalline Form L of Compound (I), Hydrochloric Acid Salt Compound (I), free base, hemihydrate crystalline form (1 g) was slurried in 6 mL of tetrahydrofuran. Next, 540 μL of 5 M HCl in isopropanol was added dropwise. The solution was kept stirring for 24 hours at 20° C. at 700 rpm. The slurry was dried in a vacuum oven without filtration at 65° C. for 48 h. A sample of the dried material (200 mg) was slurried in 1 mL of water for 12 hours at 20° C. while stirring at 700 rpm. The slurry was then dried in a vacuum oven without filtration at 65° C. for 12 hours. The solids were characterized by PXRD.

Example 15: Preparation of Crystalline Form M of Compound (I), Methane Sulfonic Acid Salt Compound (I), free base, hemihydrate crystalline form (600 mg) was slurried in 4 mL of THF at 20° C. stirring at 700 rpm. Next, 108 μL of methane sulfonic acid (15 M) was added dropwise and stirred overnight at 700 rpm at 20° C. The slurry was dried in a vacuum oven without filtration at 65° C. for 12 hours. A sample of the solid material (25 mg) was slurried in 0.5 mL of water at 20° C. while stirring at 700 rpm. The slurry was dried in a vacuum oven without filtration at 65° C. for 12 hours. Solids were then analyzed by PXRD.

Form A: Physical Properties

TABLE 14 pH-Solubility Profile of Compound (I)

| Crystalline Form A, benzenesulfonate salt | | Free base, hemihydrate crystalline form | |
|---|---|---|---|
| pH | mg/mL | pH | mg/mL |
| 1 | 0.2 | 1.49 | 7.312 |
| 2 | 0.1 | 4.40 | 0.010 |
| 3 | 0.1 | 6.76 | <0.001 |
| 4 | 0.3 | 7.51 | <0.001 |
| — | — | 9.02 | <0.001 |

The solubility of crystalline form A, benzenesulfonate salt in various solvents is provided in table 14A below.

TABLE 14A

Solubility in Solvents
Crystalline Form A, benzenesulfonate salt

| Solvent | mg/mL |
|---|---|
| N,N-dimethylformamide | >98.3 |
| Ehtanol | 4.5 |
| Acetonitrile | 1.2 |
| Isopropanol | 0.6 |
| Acetone | 0.3 |
| Water | 0.2 |

Solid State Chemical Stability of Compound (I), Benzenesulfonic Acid Salt Form A Samples of Form A of Compound (I), benzenesulfonic acid salt were stored at different conditions of temperature and humidity for 4 weeks. The physical stability, characterized by DSC, TGA, and PXRD, were measured at 2 and 4 weeks.

The solid state stability of Form A was studied by storing samples of Form A at:

(i) 5° C. in a closed container;
(ii) 25° C./60% relative humidity (RH) in open container;
(iii) 40° C./75% relative humidity in an open container; and
(iv) 50° C. in a closed container.

Samples of micronized Form A of Compound (I), benzenesulfonate were stored at different conditions of temperature and humidity for 4 weeks. The physical stability, characterized by DSC, TGA, and PXRD, were measured at 2 and 4 weeks. No change in the physical form was detected in the samples stored for 4 weeks. The data in Table 15 shows that there were no measurable changes in chemical stability of the samples.

TABLE 15

| Storage Conditions | % Assay 2 weeks | % Assay 4 weeks |
|---|---|---|
| 5° C. (control) | 99.2 | 99.2 |
| 25° C./60% relative humidity (closed) | 99.2 | 99.2 |
| 40° C./75% relative humidity (open) | 99.2 | 99.2 |
| 50° C. | 99.2 | 99.2 |
| High Intensity Light/UV | 99.3 | 99.2 |

Powder X-Ray Diffraction (PXRD)

PXRD data for Form A and Form K were collected using a Bruker D8 Discover DaVinci with XYZ Stage. The IμS X-ray generator was operated at 50 kV and 1 mA with a Cu target (CuKα radiation). Incident beam optics included Montel mirrors with a 0.3 mm collimator. Photons were counted using an Eiger2 R 500K Detector in 2D, 2θ optimized mode. Sample-to-detector distance was set to 140 mm. The samples were run for 1000 seconds in transmission, snapshot mode with the incident beam at 0° and the detector at 17.5°.

XRPD patterns for Forms C, D, E, F, G and H were collected using a PANalytical X'Pert PRO MPD Diffractometer in reflection or transmission mode, with a scanning position-sensitive detector (X'Celerator) located 240 mm from the sample. Reflection Mode used an incident bean of Cu Kα radiation produced using a long, fine-focus source and a nickel filter. The diffractometer was configured using the symmetric Bragg-Brentano geometry. A specimen of the sample was prepared as a thin, circular layer centered on a silicon zero-background substrate. Antiscatter slits (SS) were used to minimize the background generated by air. Soller slits for the incident and diffracted beams were used to minimize broadening from axial divergence. Data were collected in reflectance geometry, with a generator operated at 45 kV and 40 mA over a 2θ range of ~3-40°, with a step size of 0.017°, and a scan speed of 1.2°/minute. Transmission Mode used an incident bean of Cu radiation produced using an Optix long, fine-focus source. An elliptically graded multilayer mirror was used to focus Cu Kα X-rays through the specimen and onto the detector. A specimen of the sample was sandwiched between 3-μm-thick films and analyzed in transmission geometry. A beam-stop, short antiscatter extension, and antiscatter knife edge were used to minimize the background generated by air. Soller slits for the incident and diffracted beams were used to minimize broadening from axial divergence. Data were collected in transmission geometry, with a generator operated at 45 kV and 40 mA over a 2θ range of ~1-40°, with a step size of 0.017°, and a scan speed of 3.2°/minute.

XRPD patterns for I, J, L and M were recorded on a Bruker AXS/D8 Advance X-ray powder diffractometer with Cu Kα radiation. The diffractometer was equipped with a ceramic tube which was set at the power level of 40 kV and 40 mA, and a LYNXEYE detector. Data were collected in a Theta/2-Theta geometry, whilst spinning at a rotation speed of 15 rpm, over a 2θ range of 2-40°, with a step size of 0.05°, and a time/step of 0.5 seconds.

Differential Scanning Calorimetry (DSC)

Differential scanning calorimetry (DSC) experiments were performed using a TA Instruments Discovery DSC 2500. The sample (about 1-5 mg) was weighed in a Tzero aluminum pan. The weight of the sample was recorded accurately to a hundredth of a milligram before transferring to the DSC. The instrument was purged with nitrogen gas at 50 mL/min. Data were collected between room temperature and 350° C. at a heating rate of 10° C./min. DSC plots were generated such that the endothermic peaks pointed down.

Thermal Gravimetric Analysis (TGA)

Thermal gravimetric analysis (TGA) experiments were performed using a TA Instruments Discovery TGA 5500. The sample (about 1-10 mg) was placed in a previously cleaned and tarred platinum pan. The weight of the sample was measured accurately and recorded to a thousandth of a milligram by the instrument. The furnace was purged with nitrogen gas at 25 mL/min. Data were collected between room temperature and 350° C. at a heating rate of 10° C./min.

Moisture Sorption Isotherm

Moisture sorption isotherm data were collected on a VTI SGA-100 Symmetric Vapor Analyzer using approximately 10 mg of sample. The sample was tested at 25° C. from 95% relative humidity (RH) to 5% RH and then back to 95% RH at 5% RH decrements and increments, respectively. Equilibration at each RH was reached when the rate of 0.0010 wt. %/min for 60 minutes was achieved or a maximum of 120 minutes.

Solid-State Nuclear Magnetic Spectroscopy (ssNMR)

Carbon-13 cross polarization magic angle spinning (CP-MAS) solid-state NMR experiment was conducted on a Bruker NEO instrument operating at a proton frequency of 400 MHz. Solid samples were spun at 13 kHz in a 4 mm $ZrO_2$ rotor. The contact time was 1.5 milliseconds. The relaxation delay was maintained at $5\times{}^1H\ T_1$ of API, which was 20 seconds. Proton decoupling was applied using a TPPM sequence. The spectral sweep width was 300 ppm centered at 100 ppm. 2048 data points were acquired (giving a digital resolution of 36 Hz) and zero filled to 8192 prior to apodization. 2048 free induction decays were co-added. The spectrum was referenced indirectly to TMS using 3-methylglutaric acid (D. Barich, E. Gorman, M. Zell, and E. Munson, *Solid State Nuc. Mag. Res.,* 2006, 30, 125-129). Approximately 80 mg of sample was used for the experiment. The temperature was set to 280 K.

What is claimed is:

1. A method of treating lupus in a patient in need thereof comprising orally administering to the patient an effective amount of 2-(4-(2-(7,8-dimethyl-[1,2,4]triazolo-[1,5-a]pyridin-6-yl)-3-isopropyl-1H-indol-5-yl) piperidin-1-yl)acetamide monobenzenesulfonate having a powder x-ray diffraction (PXRD) pattern comprising 2θ values (CuKα λ=1.5418 Å) at 12.1±0.2 and 15.1±0.2, measured at a temperature of 25° C.

2. The method of claim 1, wherein the lupus is systemic lupus erythematosus.

3. The method of claim 1, wherein the lupus is cutaneous lupus erythematosus.

4. The method of claim 1, wherein the compound has a melting point in the range of 292° C. to 296° C.

5. The method of claim 1, wherein the compound has a differential scanning calorimetry (DSC) thermogram in accordance with that shown in FIG. 2.

6. The method of claim 1, wherein the compound has a thermogravimetric analysis (TGA) thermogram having weight loss of 5.5 wt % based on the weight of the compound, upon being heated to a temperature of 150° C.

7. The method of claim 1, wherein the compound has a thermogravimetric analysis (TGA) thermogram as shown in FIG. 3.

8. The method of claim 1, wherein the compound has a moisture-sorption isotherm as shown in FIG. 4.

9. The method of claim 1, wherein the compound exhibits a $^{13}C$-$^{1}H$ CPMAS solid state NMR spectrum as shown in FIG. 5.

10. A method of treating lupus in a patient in need thereof comprising orally administering to the patient an effective amount of 2-(4-(2-(7,8-dimethyl-[1,2,4]triazolo-[1,5-a]pyridin-6-yl)-3-isopropyl-1H-indol-5-yl) piperidin-1-yl)acetamide monobenzenesulfonate having a powder x-ray diffraction (PXRD) pattern comprising four or more 2θ values (CuKα λ=1.5418 Å) selected from: 6.1±0.2, 8.4±0.2, 10.1±0.2, 11.1±0.2, 12.1±0.2, 15.1±0.2, 15.6±0.2, 17.8±0.2, 18.2±0.2, and 18.7±0.2, wherein the PXRD pattern is measured at a temperature of 25° C.

11. The method of claim 10, wherein the lupus is systemic lupus erythematosus.

12. The method of claim 10, wherein the lupus is cutaneous lupus erythematosus.

13. The method of claim 10, wherein the compound has a powder x-ray diffraction (PXRD) pattern comprising five or more 2θ values (CuKα λ=1.5418 Å) selected from: 6.1±0.2, 8.4=0.2, 10.1±0.2, 11.1±0.2, 12.1±0.2, 15.1±0.2, 15.6±0.2, 17.8±0.2, 18.2±0.2, and 18.7±0.2, wherein the PXRD pattern is measured at a temperature of 25° C.

14. The method of claim 10, wherein the compound has a powder x-ray diffraction (PXRD) pattern comprising six or more 2θ values (CuKα λ=1.5418 Å) selected from: 6.1±0.2, 8.4±0.2, 10.1±0.2, 11.1±0.2, 12.1±0.2, 15.1±0.2, 15.6±0.2, 17.8±0.2, 18.2±0.2, and 18.7±0.2, wherein the PXRD pattern is measured at a temperature of about 25° C.

15. The method of claim 10, wherein the compound has a melting point in the range of 292° C. to 296° C.

16. The method of claim 10, wherein the compound has a differential scanning calorimetry (DSC) thermogram in accordance with that shown in FIG. 2.

17. The method of claim 10, wherein the compound has a thermogravimetric analysis (TGA) thermogram having weight loss of 5.5 wt % based on the weight of the compound, upon being heated to a temperature of 150° C.

18. The method of claim 10, wherein the compound has a thermogravimetric analysis (TGA) thermogram as shown in FIG. 3.

19. The method of claim 10, wherein the compound has a moisture-sorption isotherm as shown in FIG. 4.

20. The method of claim 10, wherein the compound exhibits a $^{13}C$-$^{1}H$ CPMAS solid state NMR spectrum as shown in FIG. 5.

* * * * *